United States Patent [19]

Van de Sande et al.

[11] 4,371,604
[45] Feb. 1, 1983

[54] PHOTOGRAPHIC MATERIAL SUITED FOR USE IN DIFFUSION TRANSFER PHOTOGRAPHY

[75] Inventors: Christian C. Van de Sande, Belsele; Wilhelmus Janssens, Aarschot, both of Belgium; Wolfgang Lässig; Ernst Meier, both of Munich, Fed. Rep. of Germany

[73] Assignee: Agfa-Gevaert, N.V., Mortsel, Belgium

[21] Appl. No.: 249,508

[22] Filed: Mar. 31, 1981

[30] Foreign Application Priority Data

Apr. 14, 1980 [GB] United Kingdom ............... 8012242

[51] Int. Cl.³ .................. G03C 1/40; G03C 7/00; G03C 1/10
[52] U.S. Cl. .................. 430/223; 430/218; 430/219; 430/505; 430/543; 430/559; 430/564; 430/566; 430/607; 430/955
[58] Field of Search ............... 430/223, 222, 505, 559, 430/219, 218, 212, 564, 566, 543, 607, 955

[56] References Cited

U.S. PATENT DOCUMENTS 4,232,107 11/1980 Jannssens ................ 430/223

FOREIGN PATENT DOCUMENTS 4399 3/1979 European Pat. Off. .

Primary Examiner—Richard L. Schilling
Attorney, Agent, or Firm—A. W. Breiner

[57] ABSTRACT

A photographic material for diffusion transfer photography containing a quinonoid compound, which is capable in reduced state and under alkaline conditions of releasing a photographically useful group and corresponds to one of the following general formulae:

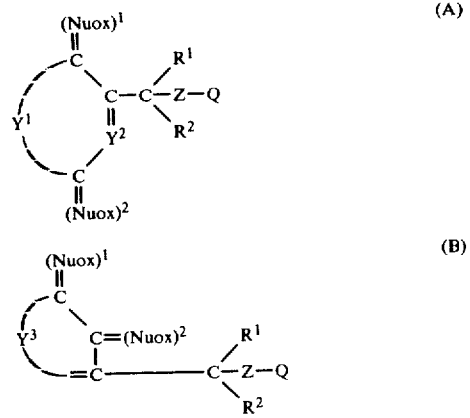

wherein:
each of $(Nuox)^1$ and $(Nuox)^2$ (same or different) represents an oxidized nucleophilic group,
Z represents a bivalent atom or bivalent atomic group, which is electro-negative,
Q together with the group Z represents a releasable photographically useful group,
$Y^1$ and $Y^2$ together represent the necessary atoms to close a p-quinonoid ring substituted with (a) directly linked monovalent organic ring or ring system substituent(s) having aromatic character,
$Y^3$ represents the necessary atoms to close a o-quinonoid ring substituted with (a) directly linked monovalent organic ring or ring system substituent(s) having aromatic character, and
each of $R^1$ and $R^2$ (same or different) represents hydrogen or a (substituted) hydrocarbon group, and at least one of $R^1$, $R^2$ and a substituent on the quinonoid ring being or carrying a ballasting group.

12 Claims, No Drawings

PHOTOGRAPHIC MATERIAL SUITED FOR USE IN DIFFUSION TRANSFER PHOTOGRAPHY

The present invention relates to quinonoid compounds and photographic material containing said compounds suited for use in diffusion transfer photography and method of diffusion transfer photography using such material.

Photographic diffusion transfer processes have been known for several years and are summarized e.g. in "Imaging Systems" by Kurt I. Jacobson and Ralph E. Jacobson (1977), The Focal Press.

Photographic image-transfer processes are based on image formation in a photosensitive image-recording layer and diffusion in an image-wise pattern of at least one substance out of said layer to form an image in an adjacent image-receiving layer and/or to leave an image-wise distributed transferred substance in said image-receiving layer.

In the generally known black-and-white DTR-process (diffusion transfer reversal process) a silver salt complex is image-wise transferred from an image-wise exposed silver halide emulsion layer to an image-receiving material wherein, with the aid of a developing agent and promoted by development nuclei, the silver salt complexes are reduced to silver.

In diffusion transfer colour processes an image-dye-providing substance is associated with a silver halide emulsion. An image-dye-providing substance, which provides a positive transferred image in an image-receiving material dependent on development of a conventional negative silver halide emulsion, is referred to as positive-working. Likewise, an image-dye-providing material, which provides a negative transferred image in an image-receiving layer dependent on development of a conventional negative silver halide emulsion, is referred to as negative-working.

Dye-diffusion systems operating with photosensitive silver halide can be carried out in a number of ways, but they are all based on the same principle, viz. the alteration in the mobility of a dye or dye-forming structural part of a compound controlled by the image-wise reduction of the photosensitive silver halide.

The image-forming substances used in colour image-transfer processes can therefore be defined as being initially mobile or initially immobile substances. These terms are generally understood to mean that the image-forming substance is either diffusible or non-diffusible in the photographic element when the latter is permeated with the processing liquid used to carry out the diffusion transfer process. The immobile substances are generally ballasted to provide sufficient immobility in the photographic element when it is permeated with the processing solution so that these substances will not diffuse substantially from their initial location. A particular class of immobile substances contains compounds that undergo a cleavage or displacement reaction to release a diffusible moiety in an image-wise pattern during the alkaline processing of image-wise exposed silver halide. The formed mobile compounds will diffuse in the photographic element until they are rendered insoluble or immobile in an image-wise pattern in a receptor material.

In accordance with the invention described in the published European patent application No. 0004399 a photographic silver halide material is provided which comprises a support carrying at least one unexposed alkali-permeable silver halide hydrophilic colloid emulsion layer which layer contains in operative contact therewith or therein a quinonoid compound, which compound is initially immobile in an alkali-permeable colloid medium and wherefrom through the reducing action of a silver halide developing agent and alkalinity a photographically useful substance, e.g. a dye, a dye precursor, a colour coupler, a fog-inhibiting compound, a development-retarding compound or another species active in photographic imaging, can be split off in diffusible state said quinonoid compound corresponding to one of the general formulae (A) and (B):

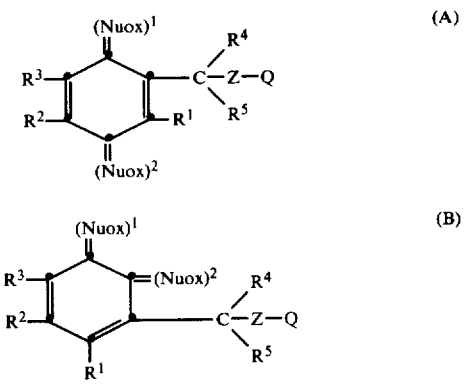

wherein:
each of $(Nuox)^1$ and $(Nuox)^2$ (same or different) represents an oxidized nucleophilic group such as a $O=$ group or $HN=$ group, Z represents a bivalent atomic group, which is electronegative with respect to the carbon atom carrying $R^4$ and $R^5$, e.g. a sulphonyl group, Q together with the Z group represents a releasable photographically useful group, e.g. a diffusible dye group, each of $R^1$, $R^2$ and $R^3$ is a mono-atomic group e.g. hydrogen, a halogen atom, or a polyatomic group, e.g. an alkyl group, an alkoxy group, an acylamino group wherein the acyl group is derived from aliphatic or aromatic carboxylic or sulphonic acids, or $R^1$ and $R^2$ together when in adjacent positions on the ring form a ring fused with the remainder of the molecule, e.g. a benzene ring, or $R^2$ and $R^3$ together form a ring fused with the remainder of the molecule, e.g. a benzene ring, and each of $R^4$ and $R^5$ (same or different) represents hydrogen or a hydrocarbon group including a substituted hydrocarbon group, e.g. an alkyl group.

In at least one of the substituents $R^1$, $R^2$, $R^3$, $R^4$ or $R^5$ a ballasting group X e.g. alkyl group of sufficient size is present to render said compound immobile in an alkali-permeable layer of the photographic material.

The reaction mechanism operative in the release of a photographically useful substance from the above mentioned quinonoid compounds consists of two stages (A) and (B):

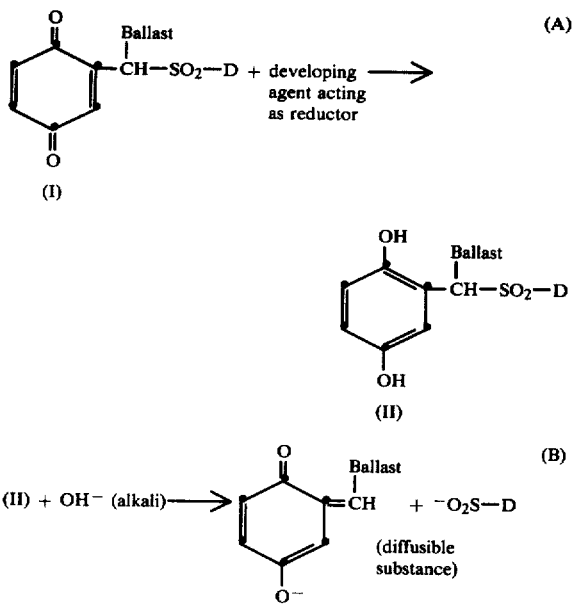

(I)

(II)

(B)

(II) + OH⁻ (alkali) ⟶ [structure] + ⁻O₂S—D
(diffusible substance)

wherein: "Ballast" stands for a ballasting group and D represents a photographically useful group e.g. a dye moiety. It is not necessary, however, that the ballasting group is linked to the =CH— group. Indeed, likewise any place on the quinone-nucleus will satisfy the purpose of obtaining an initially diffusion resistant quinonoid compound (I).

The developing agent acting as a reductor is e.g. ascorbyl palmitate optionally used in admixture with a 1-aryl-3-pyrazolidinone developing agent.

In practice there is a demand for a system wherein the photographically useful substance is split off rapidly but also substantially inversely proportional to the concentration of photoexposed silver halide. In other words when processing an image-wise exposed silver halide emulsion of the negative type in operative association with the quinonoid compound and a developing agent said diffusible substance should not be freed up to an unacceptable level in correspondence with the white areas of the photographed original or scene but should still be set free sufficiently rapidly in the less or non-exposed area where the concentration of developing agent remained high. When the reduction of compound (I) with the developing agent(s) and the hydrolysis of compound (II) prevail over the reduction of the photoexposed silver halide, too large an amount of photographically useful substance is split off in the area where it is not wanted. In the case where the photographically useful substance is a dye an undesirable dye fog is obtained in the receptor element. When, however, the reducibility of the quinonoid compound (I) is too low no acceptable dye densities are obtained within reasonable processing times required e.g. for in-camera processing applied in instant photography.

To compromise between so-called fog level and sufficient image-wise release of photographically useful substance within short processing times it would be advantageous to be able to control the reaction rate of the reactions of step (A) and/or (B). Experiments carried out showed that the reaction of step (B) under the alkaline conditions of silver halide development proceeds much faster than the reaction of step (A). Hence it was tried to control the reaction rate of reaction step (A) in order to avoid said fog thereby sacrificing as little as possible of processing speed and of image-wise release of diffusible substance.

We have found now that the direct substitution of the quinone nucleus with (a) monovalent organic ring or ring system substituent(s) having aromatic character provides a reducibility that better suits the present purpose so that by means of the thus substituted compounds within a relatively short processing time, one minute or less, an image-wise release of photographically useful substance without unacceptable fog takes place.

In accordance with the present invention a quinonoid compound having a para- or otho-quinonoid nucleus is provided corresponding to one of the general formulae (A) and (B):

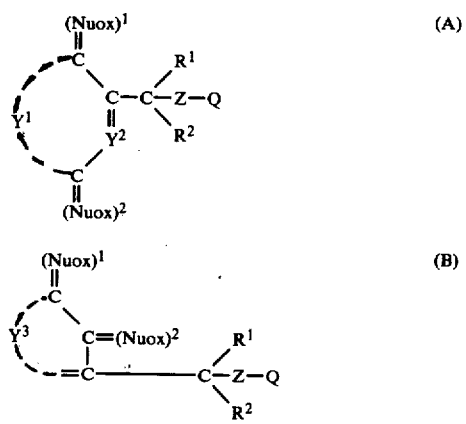

wherein:
each of (Nuox)¹ and (Nuox)² (same or different) represents an oxidized nucleophilic group e.g. a O= group or HN= group, Z represents a bivalent atom e.g. —S— or a bivalent group e.g. a sulphonyl group which is electronegative with respect to the carbon atom carrying $R^1$ and $R^2$, Q together with the group Z represents a releasable photographically useful group, e.g. a releasable group yielding a diffusible photographically useful substance as hereinbefore set forth, more particularly a diffusible dye, $Y^1$ and $Y^2$ together represent the necessary atoms to close a p-quinonoid ring substituted with (a) directly linked monovalent organic ring or ring system substituent(s) having aromatic character, $Y^3$ represents the necessary atoms to close an o-quinonoid ring substituted with (a) directly linked monovalent organic ring or ring system substituent(s) having aromatic character, each of $R^1$ and $R^2$ (same or different) represents hydrogen, a hydrocarbon group including a substituted hydrocarbon group e.g. an alkyl group including a substituted alkyl group or an aryl group including a substituted aryl group preferably one of them is a phenyl group including a substituted phenyl group, at least $R^1$, $R^2$ or a substituent on the quinonoid ring being or containing a ballasting group X e.g. an alkyl group of sufficient size to keep said compound immobile in an alkali-permeable layer of the photographic material, when said layer is contacted with an alkaline liquid.

By the wording "monovalent organic ring or ring system substituent having aromatic character" is understood a monovalent organic substituent derived from an organic substance having only carbon atoms or carbon atoms and (a) heteroatom(s) linked to each other forming a ring or ring system stabilized by resonance due to overlapping $\pi$-orbitals of alternating double bonds or of double bonds and (a) lone pair p-orbital(s) of (a) hetero atom(s), whereby the Hückel rule is obeyed. Said rule states that $(4n+2)$ electrons should be present in the overlapping orbitals, n being any positive integer here not including zero [ref.Jerry March, Advanced Organic Chemistry, Reactions, Mechanisms and Structure, 2nd Ed., McGraw-Hill Book Cy, New York, 53 (1977)].

The wording "monovalent organic ring or ring substituent having aromatic character" includes all monovalent aromatic substituents known as aryl substituents including substituted aryl substituents in which the carbon atoms of the homocyclic aromatic ring are formally included in a system of conjugated bonds as e.g. in a phenyl group, naphthyl group, anthryl group, azulenyl group including a substituted group derived therefrom e.g. an alkoxyphenyl group or an alkoxy-naphthyl group e.g. 2-methoxy-1-naphthyl or a 1-guaiazulenyl group.

Further said wording includes monovalent substituents derived from unsaturated heterocyclic ring compounds having aromatic character and which are also called heteroaromatic ring compounds. Examples of such monovalent heteroaromatic substituents are: 2-furyl, 2-thiophenyl, 2-pyrrolyl, 2-thiazolyl, 2-imidazolyl, 4-pyrazolyl, 3,5-dimethyl-2-pyrazolyl, 3-benzofuranyl or 3-indolyl.

The general formulae (A) and (B) include compounds with para- or ortho-quinonoid nucleus having one or more other substituents e.g. selected from the group of halogen, non-aromatic hydrocarbon e.g. alkyl including substituted alkyl e.g. aralkyl or alkoxy, aryloxy, acylamino wherein the acyl group is derived from aliphatic or aromatic carboxylic or sulphonic acids, amino including substituted amino e.g. alkylamino, dialkylamino or cyclic amino e.g. piperidino or morpholino, alkylthio, arylthio or sulpho. The general formulae (A) or (B) include further compounds in which the substituted para- or ortho-quinonoid nucleus forms part of a fused ring system e.g. such system including a benzene ring or bicyclo[2,2,1]heptene ring.

The said monovalent organic ring or ring system substituent having aromatic character is preferably present on the quinonoid nucleus in orthoposition to the

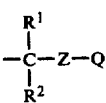

group.

Further in accordance with the present invention a photographic silver halide material is provided which material comprises a support carrying at least one unexposed alkali-permeable silver halide hydrophilic colloid emulsion layer which layer contains in operative contact therewith or therein a quinonoid compound, which compound is initially immobile in an alkali-permeable colloid medium and wherefrom through the reducing action of a silver halide developing agent and alkalinity a photographically useful substance, e.g. a dye, a dye precursor, a colour coupler, a fog-inhibiting compound, a development-retarding compound, a fixing compound or another species active in photographic imaging, can be split off in diffusible state characterized in that said quinonoid compound corresponds to one of the above general formulae (A) or (B).

The term "non-diffusing" used herein has the meaning commonly applied to the term in photography and denotes materials that in any practical application do not migrate or wander through organic colloid layers e.g. gelatin when permeated with an alkaline medium. The same meaning is to be attached to the term "immobile".

The term "diffusible" as applied to the materials of this invention has the converse meaning and denotes materials having the property of diffusing effectively through the colloid layers of the photographic elements in an alkaline medium. "Mobile" has the same meaning.

By "operative contact" is meant that in the present invention for producing diffusion transfer of an image-wise released photographically useful substance on applying an alkaline processing liquid in the presence of a photographic silver halide developing agent, said quinonoid compound can come into chemically reactive contact with the developing agent in an amount that is controlled by the image-wise developable silver halide of the image-wise photo-exposed silver halide emulsion layer.

The above quinonoid compounds may be sufficiently resistant to diffusion even when the above mentioned substituents do not contain long alkyl residues, because the molecule of the dye residue may itself be sufficiently large. In other cases, the compounds may be rendered sufficiently resistant to diffusion by providing them with sufficiently large residues.

Residues which confer diffusion resistance are residues which allow the compounds according to the invention to be incorporated in a diffusion resistant form in the hydrophilic colloids normally used in photographic materials. Organic residues which generally carry straight or branched chain aliphatic groups and which may also carry isocyclic or heterocyclic or aromatic groups generally having from 8 to 20 carbon atoms are preferably used for this purpose. These residues are attached to the remainder of the molecule either directly or indirectly, e.g. through one of the following groups: $-NHCO-$; $-NHSO_2-$; $-NR-$, in which R represents hydrogen or alkyl; $-O-$; $-S-$; or $-SO_2-$. The residue which confers diffusion resistance may in addition carry groups which confer solubility in water, e.g. sulpho groups or carboxyl groups, and these may also be present in an anionic form. Since the diffusion properties depend on the molecular size of the compound as a whole, it is sufficient in some cases, for example when the molecule as a whole is large enough, to use one or more shorter chain groups as "groups which confer diffusion resistance".

Examples of compounds particularly suited for use according to the present invention are represented in the following table 1 by their structural formula:

TABLE 1
| Compound | Structural formula |
|---|---|
| I | 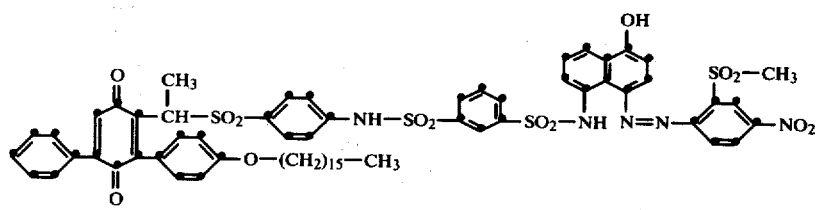 |
| II | 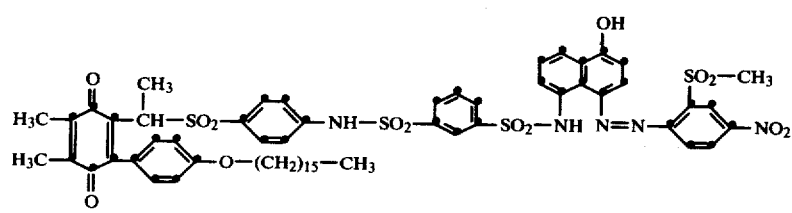 |
| III | 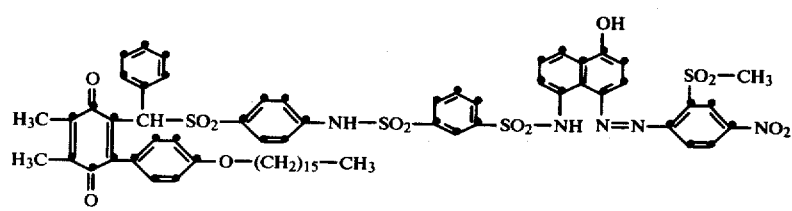 |
| IV | 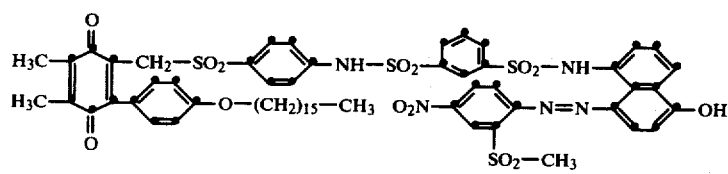 |
| V | 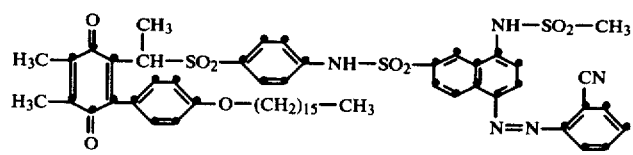 |
| VI | 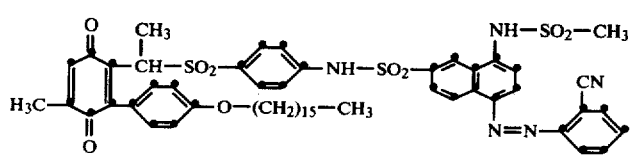 |
| VII | 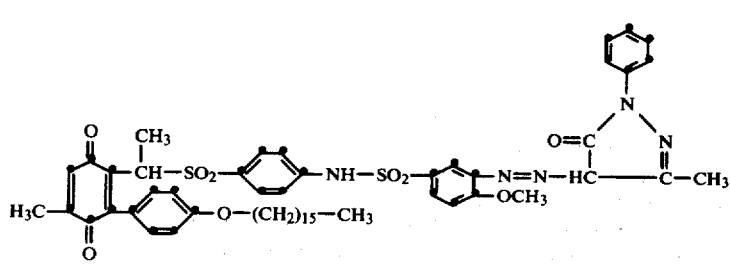 |

TABLE 1-continued
| Compound | Structural formula |
|---|---|
| VIIIa | 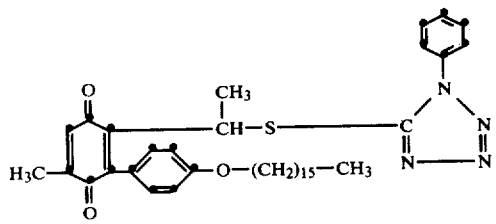 |
| VIIIb | 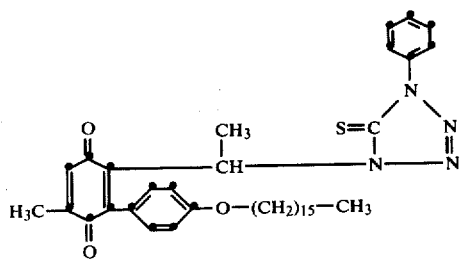 |
| IX | 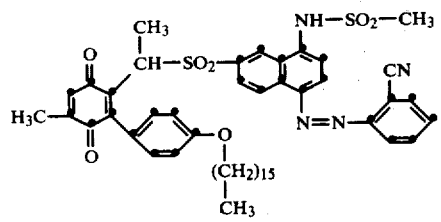 |
| X | 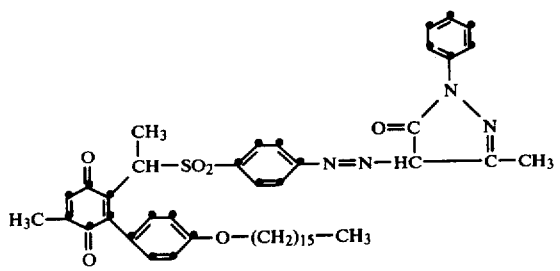 |
| XI | 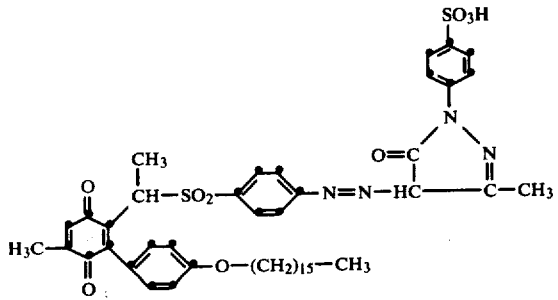 |

TABLE 1-continued

| Compound | Structural formula |
|---|---|
| XII | 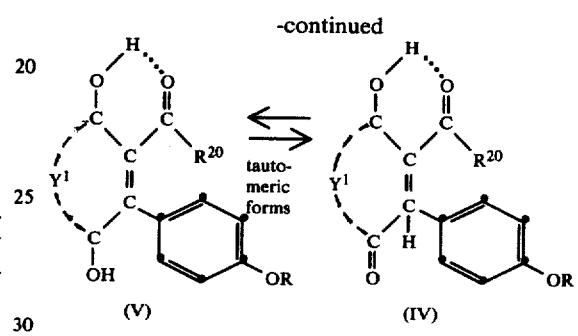 |

In the preparation of quinonoid compounds according to the present invention acylquinones are preferably used for introduction on the quinonoid nucleus of a monovalent organic ring or ring system substituent having aromatic character.

The 3-position in a 2-acyl-p-quinone has a pronounced electrophilic character and 1,4-nucleophilic additions of the type known as Michael-type additions can take place very easily. For such type of reaction reference is made to Jerry March, Advanced Organic Chemistry, Reactions, Mechanisms, and Structure, 2nd ed. Mc Graw-Hill Book Company, New York, 678–679 (1977) and C. H. Eugster and P. Bosshard, Helv.Chim. .Acta, 46, 815 (1963). The electrophilic character of acylquinones can be increased by performing the reaction with the nucleophile i.e. here the aromatic compound forming said substituent in acid medium (ref. N. Baumann, S. Fumagalli, G. Weisgerber and C. H. Eugster, Helv.Chim.Acta 49, 1794 (1966), P. Kuser, M. Inderbitzin, J. Brauchli and C. H. Eugster, ibid 54, 980 (1971), P. Kuser, E. F. Frauenfelder and C. H. Eugster Helv.Chim.Acta 54, 969 (1971); A. Braäm and C. H. Eugster, ibid 55, 974 (1972) and J. N. Tsaklidis, A. Hofer and C. H. Eugster, ibid 60, 1033 (1977).

The introduction of an aromatic substituent in the 3-position of a 2-acyl-p-quinone is illustrated by the following reaction scheme (A):

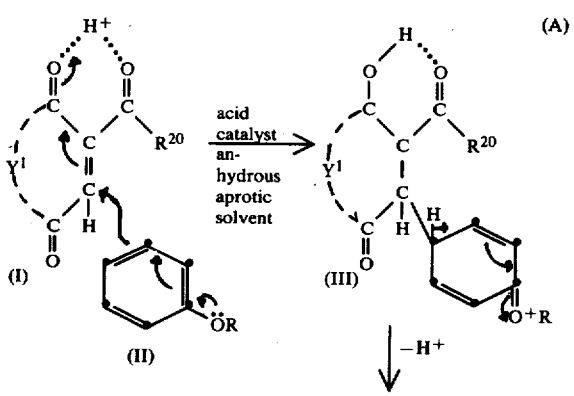

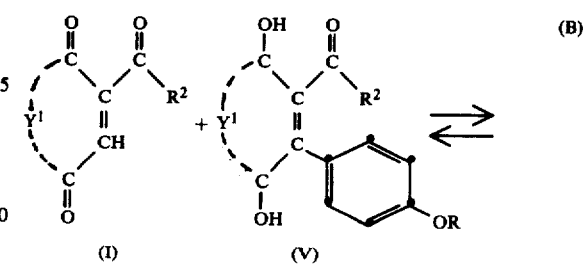

wherein:
R is alkyl and
$R^{20}$ is hydrogen, a hydrocarbon group or an alkoxy group.

From the following reaction scheme (B) it is clear that the starting compound (I) is reduced by the reaction product (V) so that a loss of starting compound (I) is unavoidable and finally a very complicated mixture of chemical compounds is obtained wherefrom the desired compound (V) is not easily isolated.

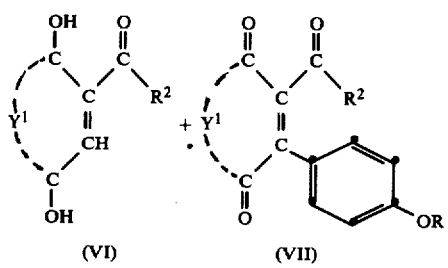

In a preferred and novel preparation technique the reaction (A) is carried out in the presence of an intentionally added oxidant capable of oxidizing acylhydroquinones. Hereby compound (VI) is immediately re-oxidized to form starting compound (I) again. One equivalent of oxidant is mostly sufficient to obtain the desired effect.

Preferred oxidants are manganese (IV) oxide and silver oxide for these compounds and their reduced forms can be easily separated. Likewise suitable are quinone compounds that in their reduced form are poorly soluble in the applied aprotic solvent such as a halogenated hydrocarbon liquid. An example thereof is 2,3-dichloro-5,6-dicyano-benzoquinone which in its reduced form is poorly soluble in 1,2-dichloroethane. Another suitable aprotic solvent is methylene chloride.

The reaction is carried out preferably at reflux temperature. More details about the substitution of particular acyl quinones with an aromatic substituent are given in the preparations hereinafter.

Preparation of compound No. I (A) 2-Acetyl-5-phenylhydroquinone

A suspension of 32.4 g of phenylhydroquinone in 30 ml of acetic acid was made. It was heated to 80° C. and boron trifluoride gas was bubbled through. After a reaction period of 4 h the reaction mixture was poured into water. The precipitation formed was suction-filtered and stirred in water whereto some sodium carbonate was added up to pH 8. The precipitate was suction-filtered again, washed with water, dried and recrystallized from toluene. Yield: 23 g of purified product. Melting point: 169° C.

(b) 2-Acetyl-3-p-hexadecyloxyphenyl-5-phenylbenzoquinone 12.25 g (0.06 mole) of compound Ia were heated in 200 ml of 1,2-dichloroethane to 60° C. with stirring. Then 13.65 g (0.06 mole) of 2,3-dichloro-5,6-dicyanoquinone were added and stirring was continued at 60° C. for 15 min. Thereupon the reaction mixture was cooled to 20° C. and filtered. To the filtrate 19.1 (0.06 mole) of n-hexadecyloxybenzene were added. Cooling was continued to 0° C. and 30 ml of trifluoroacetic acid were added.

After 15 min still 13.65 g of 2,3-dichloro-5,6-dicyanoquinone were added at about 10° C. and stirring was continued for 30 min. The reaction mixture was filtered and the filtrate washed with water till neutral, dried on sodium sulphate and concentrated with a rotary evaporator. Yield: 32.9 g. Melting point: 94°-95° C.

(c) 2-Acetyl-3-p-hexadecyloxyphenyl-5-phenylhydroquinone 13.55 g of compound Ib were dissolved in 200 ml of methylene chloride and diluted to 300 ml with ether.

A solution of 50 g of sodium hydrosulphite in 300 ml of water was added and the mixture vigorously stirred. An additional quantity of 20 g of sodium hydrosulphite was added. After 45 min of stirring the organic phase was separated, dried on sodium sulphate and concentrated by evaporation. Yield: 13.4 g of product Ic (structure confirmed by NMR). Melting point: 91° C.

(d) 2-(1-Hydroxyethyl)-3-p-hexadecyloxyphenyl-5-phenylhydroquinone 12.5 g of compound Ic was dissolved in 750 ml of methanol. A solution of 1 g of sodium borohydride in 5 ml of water was added with stirring and bubbling through nitrogen. After 30 min of stirring 8 ml of acetic acid were added. The reaction mixture was poured into 1 l of ice-water whereto 1 ml of concentrated sulphuric acid was added. The precipitate formed was filtered with suction, washed until neutral and dried. Yield: 12.4 g of product Id (structure confirmed by NMR). Melting point: 85°-86° C.

(e) Hydroquinone form of compound I 5.4 g of compound Id were dissolved in 150 ml of acetic acid at 60° C. forming solution A.

A mixture of 11 g of compound 5a prepared as described in the published European patent application 0.004.399, 1 g of sodium acetate, 180 ml of acetic acid, 120 ml of water was heated to 50° C. and solution A was added. The reaction mixture was stirred at 60° C. for 3 h. After cooling the precipitate formed was suction-filtered, washed with a 1:1 mixture by volume of methanol/water and dried. Yield: 14 g of product Id.

(f) Compound I 14 g of compound Ie were dissolved in 100 ml of ethylene glycol monomethyl ether at 50° C. Then 2.5 g of p-benzoquinone were added and stirred at 60° C. for 30 min. The reaction mixture was poured into 300 ml of water and acidified with a few drops of hydrochloric acid. The precipitate was suction-filtered, washed with a 1:1 mixture by volume of methanol/water, dried and purified by preparative column-chromatography on silica gel by means of a mixture of methylene chloride/ethyl acetate (95/5 by volume) as the eluent. Yield of purified product: 4.6 g.

Preparation of compound No. II (a) 2,3-dimethyl-6-acetyl hydroquinone 276 g (2 mole) of 2,3-dimethyl-hydroquinone were suspended in 300 ml of acetic acid and heated to 80° C. with stirring. Through the obtained solution boron trifluoride was bubbled whereby care was taken that the temperature did not exceed 100° C. The reaction mixture was stirred at 120° C. for 3.5 h and then poured into 4 l of ice-water containing 500 g of dissolved sodium acetate. This mixture was stirred for 12 h till the precipitate could be separated by suction. This precipitate was then treated with 3 l of water whereto enough sodium hydrogen carbonate was added to reach a final pH of 7.5. The precipitate was suction filtered again, washed with water till neutral and recrystallized from toluene. Yield: 230 g. Melting point: 151° C. (structure confirmed by NMR).

(b) 2,3-Dimethyl-5-p-hexadecyloxyphenyl-6-acetylhydroquinone 36 g (0.2 mole) of compound II were dissolved in 800 ml of hot methylene chloride with stirring. A mixture of 100 g of precipitated manganese(IV) dioxide and 100 g of sodium sulphate (anhydrous) were added. The reaction mixture was refluxed for about 1 h till oxidation into the quinone form of compound IIa. The reaction mixture was cooled and the non-reacted manganese(IV) dioxide removed by suction-filtering.

62 g (0.195 mole) of n-hexadecyloxybenzene were added and stirring was continued till complete dissolution. The reaction mixture was cooled just below 2° C. and 100 ml of trifluoro acetic acid were added dropwise whereby care was taken that the reaction temperature did not exceed 5° C. After a further stirring period of 30 min still 50 g of manganese(IV) dioxide were added. Stirring was continued for 30 min. Then an additional portion of 25 ml of trifluoroacetic acid was added and stirring continued till completion of the reaction, which took about 1 h. Thereupon 600 ml of ether were added and the manganese(IV) dioxide was removed by suction-filtering.

The filtrate was washed twice with 1 l of water and stirred with 300 g of sodium hydrosulphite for 30 min. The organic liquid was separated and washed twice with water. Drying proceeded with sodium sulphate, whereupon the solvent was evaporated. Yield: 87 g. Melting point: 68° C. (structure was confirmed by NMR).

(c) 2,3-Dimethyl-5-p-hexadecyloxyphenyl-6-(1-hydroxyethyl)-hydroquinone 98.5 g of compound IIb were reduced at 80° C. for 3 h in 600 ml of anhydrous ethanol with hydrogen at a pressure of 105 kg/sq.cm by means of Raney-nickel as a catalyst.

The latter was removed by filtering, the filtrate cooled and the precipitate formed suction-filtered and dried. Yield: 70 g. Melting point: 76.5° C. (structure was confirmed by NMR).

(d) Hydroquinone form of compound II 30.6 g of compound 5a prepared according to published European patent application 0.004.399, 3 g of sodium acetate, 500 ml of acetic acid and 350 ml of water were stirred at 60° C.

To the obtained solution 15 g of compound IIc dissolved at 50° C. in 500 ml of acetic acid were added. The mixture was stirred at 60° C. for 4 h and then cooled. The formed precipitate was suction-filtered and washed with a mixture of methanol/water 1:1 by volume. Yield: 38.5 g.

(e) Compound II 38.5 g of compound IId were dissolved at 60° C. in 400 ml of ethylene glycol monomethyl ether and 5 g of p-benzoquinone added thereto. The reaction mixture was heated at 60° C. for 1 h and poured into 800 ml of water whereto 5 ml of concentrated hydrochloric acid were added. The precipitate formed was suction-filtered, washed with a mixture of methanol/water 1:1 by volume, dried and purified by preparative column-chromatography on silicagel by means of a mixture of methylene chloride/ethyl acetate (90/10 by volume) as the eluent.

Preparation of compound III (a) 2,3-Dimethyl-6-benzoyl-hydroquinone 138 g (1 mole) of 2,3-dimethylhydroquinone and 244 g (2 mole) of benzoic acid were mixed thoroughly and whilst stirring heated gradually up to 150° C. while introducing boron trifluoride. The stirring of the reaction mixture was continued for 2 h. Thereupon the reaction mixture was cooled to 90° C. and poured into a solution of 332 g (4 mole) of sodium acetate in 3 l of water whilst vigorously stirring.

The precipitate was put into ether and washed with an aqueous solution of sodium acetate whereupon sodium hydrogen carbonate was added up to alkaline reaction. Then the mixture was washed with water to neutral. The organic liquid was separated and dried on sodium sulphate. After removal of the ether by evaporation 53 g of compound IIIa were obtained. Melting point: 129.5° C.(structure confirmed by NMR).

(b) 2,3-Dimethyl-5-p-hexadecyloxyphenyl-6-benzoylhydroquinone 24.2 g (0.1 mole) of compound IIIa were dissolved in 400 ml of 1,2-dichloroethane and with 50 g of freshly precipitated manganese(IV) dioxide in the presence of 50 g of sodium sulphate oxidized into its quinone form. The reaction mixture was boiled with reflux for 30 min. After cooling the non-reacted manganese(IV) was filtered off with suction.

To the filtrate 31 g (0.097 mole) of n-hexadecyloxybenzene was added whilst stirring till dissolution. The reaction mixture was cooled just below 2° C. and 75 ml of trifluoroacetic acid were added in 20 min so that the temperature did not raise above 5° C. Stirring was continued for 2.5 h and again 50 g of manganese(IV) dioxide were added and stirring continued overnight at 20° C.

The solids were removed by suction filtering and to the filtrate an equal volume of ether was added. The reaction product was reduced to the hydroquinone form with 150 g of sodium hydrosulphite dissolved in 900 ml of water.

The reduction proceeded for 30 min whilst stirring. The organic liquid was separated, washed to neutral and dried on sodium sulphate. The ether was removed in a rotary evaporator.

Crystallization proceeded from 280 ml of CLAIRSOL 300 (trade name). Yield: 38 g. Melting point: 93° C. (structure confirmed by NMR).

CLAIRSOL 300 is a trade name of Carless Solvent Ltd. London Eng. for a petroleum fraction boiling between 140° C.–156° C.

(c) 2,3-Dimethyl-5-p-hexadecyloxyphenyl-6-(1-hydroxybenzyl)hydroquinone 33.5 g (0.06 mole) of compound IIIb was dissolved in 900 ml of methanol under nitrogen protection. A solution of 2.63 g of sodium borohydride in 15 ml of water was dropwise added. After 30 min stirring 45 ml of acetic acid were added dropwise and the reaction mixture poured into 1 l of ice-water containing 1 ml of concentrated sulphuric acid. The precipitate was separated by suction filtering and dried. Yield: 34 g (structure confirmed by infra-red spectroscopy).

(d) Hydroquinone form of compound III 8.4 g (15 millimole) of compound IIIc were dissolved in 80 ml of acetic acid at 60° C. forming solution A.

A mixture of 14.5 g of compound 5a prepared as described in the published European patent application 0.004.399, 1.5 g of sodium acetate, 250 ml of acetic acid, 125 ml of water was heated to 50° C. and added to solution A. The reaction mixture was stirred for 8 h at 70° C. After cooling the precipitate formed was suction-filtered, washed with a mixture of methanol/water (1:1 by volume) and dried. Yield: 16.5 g.

(e) Compound III 49.5 g of compound IIId were dissolved at 60° C. in 400 ml of ethylene glycol monomethyl ether. Then 7.5 g of p-benzoquinone were added and stirred at 60° C. for 30 min. The reaction mixture was cooled to 40° C.

and whilst stirring poured into 1 l of water acidified with 10 ml of concentrated hydrochloric acid. The precipitate was suction filtered, washed with a mixture of methanol/water (1:1 by volume) and dried. The product was purified by preparative column-chromatography on silica gel by means of methylene chloride/ethyl acetate (95/5) as the eluent. Yield: 26.3 g.

Preparation of compound No. IV (a) 2,3-dimethyl-6-carboxy-hydroquinone 53 g of 2,3-dimethylhydroquinone were mixed with 265 g of dry potassium carbonate. This mixture was subjected to a $CO_2$ treatment in a high-pressure autoclave at 175° C. under a pressure of 84 kg/sq.cm for 8 h.

The obtained reaction mixture was ground under nitrogen, dissolved in 2.3 l of water, acidified with 120 ml of acetic acid and finally strongly acidified with hydrochloric acid.

The precipitate formed was suction-filtered and dried. Thereupon it was dissolved in 400 ml of ether, filtered and dried on sodium sulphate. The filtrate was concentrated in a rotary evaporator. Yield: 49.6 g. Melting point: 213° C. The structure of compound IVa was confirmed by NMR.

(b)

45.5 g (0.25 mole) of compound IVa were dissolved in 100 ml of anhydrous methanol. Dry hydrogen chloride gas was bubbled through until saturation whereupon the reaction mixture was refluxed for 7 h.

The reaction mixture was concentrated till dry in a rotary evaporator. The solid residue left was dissolved in 500 ml of ether, washed first with water, then with 100 ml of aqueous 10% by weight solution of sodium hydrogen carbonate and finally once more with water. The solution was dried on sodium sulphate and evaporated till dry in a rotary evaporator. Yield: 30.4 g. Melting point: 150° C. The structure was confirmed by NMR.

(c) 2,3-Dimethyl-5-p-hexadecyloxyphenyl-6-methoxycarbonylhydroquinone 24.5 g (0.125 mole) of compound IVb were dissolved in 500 ml of methylene chloride. Then 62.5 g of manganese(IV) dioxide together with 62.5 g of sodium sulphate were added with stirring and heating. The mixture was refluxed till completion of the oxidation.

38.75 g of n-hexadecyloxybenzene were added and stirring was continued till dissolution. The excess of manganese(IV) dioxide was removed by filtering. The filtrate was cooled to 2° C. and 65 ml of trifluoroacetic acid were dropwise added.

After 1 h of reaction at a temperature below 5° C. 65 g of manganese (IV) dioxide were added and stirred in an ice-bath for 1 night.

The reaction mixture was filtered. The filtrate was diluted with 1 l of ether. Thereto 1 l of water and 50 g of sodium hydrosulphite were added with stirring. After 30 min of stirring the aqueous layer was removed. Again 2 l of water were added and sodium hydrogen carbonate was added with stirring up to pH 7. The aqueous layer was removed and the ether layer was washed again with water and dried on sodium sulphate. The ether was evaporated in a rotary evaporator and the product formed recrystallized from ethanol. Yield: 48.65 g (structure confirmed by NMR).

(d) 2,3-Dimethyl-5-p-hexadecyloxyphenyl-6-hydroxymethylhydroquinone

The following reaction was carried out in glassware that had been dried at 120° C.

6.3 g of lithium aluminium hydride (0.165 mol) were dissolved in 400 ml of dry ether. Under nitrogen gas a solution of 25.6 g (0.05 mole) of compound IVc in 300 ml of dry ether was added slowly such that the mixture boiled gently with reflux.

After the addition of compound IVc the reaction mixture was refluxed for 2 h. The excess of lithium aluminium hydride was decomposed with 45 ml of acetic acid and the reaction mixture neutralized with 40 ml of acetic acid. Thereupon 200 ml of a 5% by weight aqueous solution of sulphuric acid were added. The ether layer was separated, washed with water till neutral and dried on sodium sulphate. In a rotary evaporator the ether was removed and the residue left dried under reduced pressure in the presence of potassium hydroxide. Crystallization proceeded from 200 ml of CLAIRSOL 300 (trade name). Yield: 19.4 g. (structure confirmed by NMR).

(e) Hhydroquinone form of compound IV

A suspension of 8 g of compound IVd in 80 ml of cold acetic acid was made and added at 60° C. to a mixture of 13.8 g of compound 5a prepared according to the published European patent application 0.004.399 1.3 g of sodium acetate, 240 ml of acetic acid and 120 ml of water. The reaction mixture was stirred at 60° C. for 4 h. After cooling the precipitate was separated by suction and washed with a mixture 1:1 by volume of methanol/water. Yield: 19 g.

(f) Compound IV 25 g of compound IVe were dissolved in 200 ml of ethylene glycol monomethyl ether at 60° C.

4 g of p-benzoquinone were added and the reaction mixture was heated at 60° C. for 1 h. Then it was cooled, poured into water and acidified with a few drops of hydrochloric acid. The precipitate formed was suction-filtered and washed with a 1:1 by volume mixture of methanol/water. After drying the product was purified by preparative column-chromatography on silicagel with a mixture of methylene chloride/ethyl acetate (95/5 by volume) as the eluent. Yield: 9.3 g.

Preparation of compound No. V (a) 1-methylsulphonylamino-4-(2-cyanophenyl-azo)-7-sulphonaphthalene To 600 ml of pyridine 223 g (1 mole) of 1-amino-7-sulpho-naphthalene were added. Then 92.8 ml (1.2 mole) of methylsulphonyl chloride were dropwise added with stirring and the temperature was allowed to rise to 60° C. Stirring was continued for 30 min and the reaction mixture poured into a mixture 2 kg of ice and water to reach a temperature of 5° C., which temperature was suited for effecting diazotisation.

Diazotisation of o-aminobenzonitrile: 130 g (1.1 mole) of o-aminobenzonitrile were dissolved in 2 l of water whereto 275 ml of concentrated hydrochloric acid were added at 50° C. This solution was cooled to 0° C. Diazotation was effected by dropwise addition of a solution of 79.35 g (1.15 mole) of sodium nitrite dissolved in 200 ml of water at 0° C. The reaction mixture was stirred at 0° C. for 30 min.

The azo-coupling proceeded at 5° C. by adding the diazonium salt solution with stirring to the solution of 1-methylsulphonylamino-7-sulpho-naphthalene in pyridine. Stirring was continued and 400 ml of concentrated hydrochloric acid were added.

The precipitate was suction-filtered, washed trice each time with 500 ml of 10% by weight aqueous sodium chloride solution and dried. Yield: 395 g (sodium chloride content: 25% by weight).

(b) 1-Methylsulphonylamino-4-(2-cyanophenylazo)-7-chlorosulphonyl-naphthalene 430 g of the reaction product Va were stirred in 2 l of 1,2-dichloroethane and heated to remove the residual water. The mixture was cooled to 40° C. whereupon 100 ml of N-methylpyrrolidinone were added. Then 300 ml of phosphorous oxychloride were added dropwise till the temperature reached 50° C. Stirring was continued at 50° C. for 2 h. After cooling over night, the precipitate was suction-filtered and washed trice each time with 300 ml of methylene chloride. After drying, the precipitate was stirred in 2 l of water, separated again and dried. Yield: 163 g.

(c) 1-methylsulphonylamino-4(2-cyano-phenylazo)-7-(p-sulphino-phenylsulphamyl)-naphthalene To a solution of 52.5 g of p-aminobenzene sulphinic acid and 96 g of potassium carbonate in 850 ml of water first 1 l of acetone was added and then portionwise 157 g of compound Vb with stirring. Thereupon, the mixture was stirred for 1 h, poured into 2.5 l of water and acidified with 100 ml of concentrated hydrochloric acid. The precipitate formed was sucked off, washed with methanol and dried. Yield: 160 g.

(d)

7.2 g of compound IIc were dissolved at 60° C. in 100 ml of acetic acid forming solution A.

At 50° C. a solution was made of 12.7 g of compound Vc, 1.5 g of sodium acetate, 270 ml of acetic acid and 180 ml of water. Said solution was added to solution A and the mixture stirred at 60° C. for 11 h. After cooling, the precipitate was suction-filtered, washed with a mixture of methanol/water (1:1 by volume) and dried. Yield: 12 g.

(e) Compound V 12 g of compound Vd were dissolved at 60° C. in 120 ml of ethylene glycol monomethyl ether. Then 2 g of p-benzoquinone were added and the reaction mixture was stirred at 60° C. for 1 h. Thereupon the mixture was poured into 400 ml of water acidified with a few drops of hydrochloric acid. The precipitate formed was filtered with suction, washed with water, dried, and purified by preparative column chromatography on silica gel by means of a mixture of methylenechloride/ethyl acetate (85/15 by volume) as the eluent. Yield: 5.5 g.

Preparation of compound No. VI-First Mode (a) 2-Acetyl-5-methyl-hydroquinone 496 g (4 mole) of methylhydroquinone and 512 ml of acetic acid were heated at 80° C. with stirring. Boron trifluoride gas was bubbled through whereby the reaction temperature reached 120° C. Stirring was then continued and the reaction temperature kept at 120° C. for 1 h. Whilst vigorous stirring the reaction mixture was poured into 6 l of ice-water containing 1 kg of sodium acetate. Stirring was continued for 12 h whereupon the precipitate formed was filtered off, first washed by stirring in water containing some sodium carbonate and then with pure water, and finally dried. Purification proceeded by extraction with CLAIRSOL 300 (trade name). Yield: 400 g. Melting point: 144°-146° C.

(b) 2-Acetyl-4-p-hexadecyloxyphenyl-5-methyl-hydroquinone 166 g (1 mole) of compound VIa were dissolved in 4 l of methylene chloride. Then 500 g of precipitated manganese (IV) dioxide and 500 g of sodium sulphate were added with stirring. The reaction mixture was refluxed with stirring for 90 min and filtered through a layer of sodium sulphate. To the filtrate 310 g (0.975 mole) of n-hexadecyloxybenzene were added and stirring was continued till complete dissolution. The solution was cooled just below 2° C. with stirring and 500 ml of trifluoro acetic acid were dropwise added such that the temperature did not rise above 5° C. After a further stirring period of 1 h, still 300 g of manganese (IV) dioxide were added. Stirring was continued for 2 h. The precipitate of manganese (IV) dioxide was separated by suction and the filtrate concentrated to 1 l in a rotary evaporator. The concentrated filtrate was diluted with 2.5 l of ethyl acetate and 2.5 l of water, and treated with 1 kg of sodium hydrosulphite.

After being stirred for 15 min the organic liquid layer was separated, washed first with 2.5 l of water containing 140 g of sodium hydrogen carbonate and subsequently twice with 2 l of 15% by weight aqueous sodium chloride solution and dried with sodium sulphate.

The solid product was obtained by evaporating the volatile solvent in a rotary evaporator. Recrystallization from 1.8 l of ethanol yielded 306 g of compound VIb. Melting point: 68° C.

(c) 2-(1-Hydroxyethyl)-3-p-hexadecyloxyphenyl-5-methyl-hydroquinone 96.5 g of compound VIb dissolved in 600 ml of anhydrous ethanol were reduced at 70°-75° C. under a hydrogen pressure of 105 kg/sq.cm in the presence of Raney-nickel for 3 h.

The catalyst was removed by filtering and the filtrate cooled in ice. The precipitate formed was suction-filtered, washed twice with cold ethanol and dried under reduced pressure. Yield: 81.6 g. Melting point: 75° C. (structure confirmed by NMR).

(d) Hydroquinone form of compound VI 42.5 g of compound Vc, 5 g of sodium acetate, 750 ml of acetic acid and 500 ml of water were dissolved at 60° C. forming solution A.

24.2 g of compound VIc were dissolved at 50° C. in 200 ml of acetic acid and added to solution A. The reaction mixture was stirred at 60° C. for 12 h. After cooling, the precipitate was filtered with suction, washed with a mixture of methanol/water (1:1 by volume) and dried. Yield: 47.5 g.

(e) Compound VI 47.5 g of compound VId were dissolved at 60° C. in 550 ml of ethylene glycol monomethyl ether. Then 8 g of p-benzoquinone were added and the reaction mixture was stirred at 60° C. for 1 h. After cooling to 40° C. the reaction mixture was poured with stirring into 1.5 l of water whereto 10 ml of concentrated hydrochloric acid were added. The formed precipitate was suction-filtered, washed with a mixture of methanol/water (1:1 by volume) dried and purified by preparative column chromatography on silica gel by means of a mixture of methylene chloride/ethyl acetate (90/10) as the eluent.

Yield: 25 g. Melting point (unsharp): 100° C.

Preparation of compound VI-Second mode (f)
2-(1-p-aminophenylsulphonylethyl)-3-p-hexadecyloxyphenyl-5-methyl-benzoquinone 51 g of p-aminobenzene-sulphinic acid and 121 g of compound VIc were stirred at 60° C. in a mixture of 1500 ml of acetic acid and 150 ml of water. To the mixture 15 ml of concentrated sulphuric acid were added at 60° C. and stirring was continued for 15 min. Oxidation of the hydroquinone proceeded by adding 230 ml of an aqueous iron (III) chloride solution (3.5 moles per liter) and stirring at 60° C. for 1 h. Thereupon 1500 ml of water were added to the reaction mixture at room temperature, and the precipitate was separated by suction-filtering and washed with water.

After recrystallization from benzine 64 g of compound VIf were obtained. Melting point: 124° C.

(g) Compound VI 12.4 g of compound VIf and 9.9 g of compound Vb were stirred at 20° C. in a mixture of 150 ml of methylene-chloride and 3 ml of pyridine for 90 min.

The formed precipitate was separated by suction-filtering and washed with methylene chloride. The filtrates were concentrated to dryness and the residue purified by preparative column chromatography under pressure on silicagel as the adsorbent and by means of a mixture of methylene chloride/ethyl acetate (85/15 by volume) as an eluent. Yield: 5.4 g.

Preparation of compound VII (a) Hydroquinone form of compound VII 208 g of compound 1e prepared as described in the published European patent publication No. 0.004.399, 20 g of sodium acetate, 1.7 l of acetic acid and 1 l of water were stirred at 60° C. To the obtained mixture 96.8 g of compound VIc dissolved at 50° C. in 600 ml of acetic acid were added. The reaction mixture was kept at 60° C. for 6 h. Thereupon the reaction mixture was cooled and the formed precipitate was suction-filtered, washed with a mixture of methanol/water 1:1 by volume and dried.

Crystallization proceeded by dissolving the product at 80° C. in 1 l of ethylene glycol monomethyl ether, hot filtering and heating again to 80° C. After the addition of 100 ml of water and stirring, the mixture was cooled. The obtained precipitate was suction-filtered and washed with methanol. Yield: 98.5 g. Melting point: 138° C.

(b) Compound VII 98.5 g of compound VIIa were dissolved in 1 l of ethylene glycol monomethyl ether and 15 g of p-benzoquinone were added at 60° C. The reaction mixture was stirred at 60° C. for 1 h and cooled to 30° C. The precipitate formed was suction-filtered, washed with a mixture of methanol/water 1:1 by volume and dried. Yield: 92.5 g. Melting point: 139° C.

Preparation of compounds VIIIa and VIIIb (a) hydroquinone forms 12.1 g (0.025 mole) of compound VIc and 4.45 g (0.025 mole) of 1-phenyl-5-mercapto-tetrazole were dissolved in 90 ml of acetic acid and heated for 7 h at 60° C. The reaction mixture was concentrated by evaporation under vacuum at 30° C. The thick oily residue was subjected to prolonged vacuum treatment at 30° C. in order to remove any traces of residual water and acetic acid. Yield: 16 g. By thin layer chromatography was established that neither compound VIc nor 1-phenyl-5-mercaptotetrazole were still present. It also showed that two hydroquinones were formed, the mixture of which was subjected to oxydation without separation.

(b) compounds VIIIa and VIIIb 3.2 g (0.005 mole) of the above mixture was dissolved in 50 ml of dichloromethane at 40° C. After addition of 0.54 g (0.005 mole) of p-benzoquinone the reaction mixture was stirred at 40° C. for 30 minutes. The reaction mixture was then concentrated under vacuum and subjected to preparative column chromatography on silicagel (eluent: dichloromethane) yielding 0.85 g of compound VIIIa and 0.95 g of compound VIIIb. Differentiation of both isomers could be made by means of $^{13}C$ nuclear magnetic resonance, more particularly the shift of the signal from the tetrazolic carbon atom:

compound VIIIa: 154.15 ppm
compound VIIIb: 162.00 ppm

Preparation of compound IX (a)
1-methylsulphonylamino-4(2-cyanophenylazo)-7-sulphinonaphthalene 252 g (2 moles) of anhydrous sodium sulphite were dissolved at 80° C. in 2.4 l of water. At 80° C. 448.5 g (1 mole) of compound Vb were added portionwise to the sulphite solution and the pH was kept at 8 by simultaneous addition of a 10% by weight aqueous solution of sodium hydroxide. The reaction mixture was cooled to 15° C. by adding ice and thereupon the pH lowered to 5.4 with 120 ml of acetic acid. The precipitate formed was separated by suction-filtering and dried. Yield: 340 g.

(b) Hydroquinone form of compound IX 97 g (0.2 mole) of compound VIc and 91 g (0.208 mole) of compound IXa were stirred at 70° C. in a mixture of 1.8 ml of acetic acid and 300 ml of water. The reaction was completed within 1 h. Thereupon the mixture was cooled to 50° C. and the precipitate formed separated by suction-filtering, washed with a mixture of methanol-water (1/1 by volume) and dried. Yield: 145 g.

(c) Compound IX 145 g (0.165 mole) of compound IXb and 45 g (0.18 mole) of tetrachloro-p-benzoquinone were added to 1 l of ethylene glycol monomethyl ether and heated at 70° C. whilst stirring for 30 min. The reaction mixture was cooled to 30° C. whereupon 250 ml of water were added slowly. The formed precipitate was separated by suction-filtering and dried. The compound was purified by preparative column-chromatography under pressure on silicagel as adsorbent and with a mixture of methylene chloride/ethyl acetate (90/10 by volume) as an eluent. Yield: 110 g.

Preparation of compound X (a)
1-phenyl-3-methyl-4-(2-methoxy-5-sulphino-phenylazol)-pyrazoline-5-one 23.3 g of 1-phenyl-3-methyl-4-(2-methoxy-5-chlorosulphonyl-phenylazo)-pyrazoline-5-one prepared as intermediate product 5.1 according to the published European Patent Application No. 0 004 400 were stirred in a mixture of 200 ml of water and 100 ml of acetone. Then, 12.6 g of anhydrous sodium sulphite were added and the reaction mixture having a pH 10.5 was refluxed with stirring. During this operation the pH decreased slowly and a 10% by weight aqueous sodium hydroxide solution was added to keep the pH at 8. After 6 h of refluxing, the reaction mixture was cooled to 50° C., acidified with 10 ml of concentrated hydrochloric acid and suction-filtered in hot state. The precipitate was washed with a mixture of acetone/water (1/1 by volume) until free of acid and dried. Yield: 17.2 g. Melting point: above 260° C.

The same compound Xa can be prepared likewise according to the following method:

400 ml of water were mixed with 100 ml of concentrated hydrochloric acid and cooled to 0° C. Then 105 g of 3-amino-4-methoxy-benzenesulphinic acid sodium salt were added and the diazotisation was carried out at a temperature below 5° C. by dropwise adding a solution of 36 g of sodium nitrite in 150 ml of water.

The reaction mixture was stirred for still 30 min and the excess of nitrite decomposed with ureum.

91.5 g of 1-phenyl-3-methyl-pyrazoline-5-one were added to a solution of 54 g of sodium hydroxide in a mixture of 200 ml of water and 800 ml of acetone cooled at 0° C. To the solution the diazotisation-solution was added dropwise whilst the reaction mixture was kept at a temperature not exceeding 10° C. Stirring was continued for 30 min whereupon the reaction mixture was acidified with 25 ml of acetic acid; the precipitate formed was filtered with suction, washed with a mixture of acetone/water (2/1 by volume) and dried. Yield: 114 g.

(b) Hydroquinone form of compound X 48.4 g (0.1 mole) of compound VIc were stirred at 70° C. in a mixture of 400 ml of acetic acid and 100 ml of water. After cooling to 50° C. the formed precipitate was separated by suction-filtering, washed with a mixture of methanol/water (3/1 by volume) and dried. Yield: 74.2 g. Purification proceeded by dissolving the product in a mixture of 550 ml of ethylacetate and 200 ml of methanol and adding 35 ml of water. The formed crystalline product is filtered off and washed with methanol. Yield: 54.5 g. Melting point: 146° C.

(c) Compound X 98.5 g of compound Xb were stirred at 80° C. in 1 l of ethylene glycol monomethyl ether. To the obtained solution 15 g of p-benzoquinone were added and the reaction mixture was heated at 80° C. for 30 min. Upon cooling to 30° C. the formed precipitate was filtered off, washed with a mixture of methanol/water (1/1 by volume) and dried. Yield: 92.5 g. Melting point: 139° C.

Preparation of compound XI

To a solution of 24.8 g of compound VIf in 200 ml of acetone 12 ml of concentrated hydrochloric acid were added. The solution was cooled to 5° C. and the diazotisation carried out with a solution of 3.2 g of sodium nitrite in 20 ml of water. The reaction mixture was diluted with 40 ml of water. The diazotisation-solution was added whilst stirring at 5° C. to the following mixture:

22.4 g 1-(4-sulphophenyl)-3-methyl-pyrazoline-5-one
600 ml of methanol
20 g of anhydrous sodium acetate
40 ml of pyridine The reaction mixture was stirred for 1 h and the precipitate formed separated by suction-filtering, first washed with acetone and subsequently with methanol, and dried. Purification proceeded by preparative column-chromatography under pressure on silicagel as an adsorbent and by means of a mixture of methylene chloride/methanol (80/20 by volume) as an eluent. Yield: 3.5 g.

Preparation of compound XII (a)
2-[1-(3-amino-4-methoxy-phenylsulphonyl)-ethyl]-3-p-hexadecyloxyphenyl-5-methyl-benzoquinone.

97.5 g (0.2 mole) of compound VIf in hydroquinone form and 54.6 g (0.2 mole) of 3-amino-4-methoxy-benzenesulphinic acid were stirred in a mixture of 1200 ml of acetic acid and 120 ml of water. Whilst stirring 12 ml of concentrated sulphuric acid were dropwise added at 60° C. within 30 min. Oxidation of the hydroquinone proceeded by dropwise adding 120 ml of aqueous iron-(III) chloride (3.5 moles per liter).

The reaction mixture was stirred at 60° C. for 1 h whereupon 1200 ml of water were added. After cooling the mixture, the formed precipitate was separated by suction-filtering, washed until neutral and dried. Recrystallisation proceeded from 350 ml of ethyl acetate.

Yield: 78 g. Melting point: 168° C.

(b)

26 g of compound XIIa were stirred in a mixture of 200 ml of acetone and 12 ml of concentrated hydrochloric acid. Diazotisation was effected at 5° C. by dropwise adding 3.2 g of sodium nitrite dissolved in 20 ml of water. After this addition stirring was continued for 30 min.

The obtained diazotisation-solution was added whilst stirring at 5° C. to a solution of 11 g of 1-phenyl-3-(carboxylic acid β-methoxyethyl ester)-pyrazoline-5-one in a mixture of 200 ml of acetone and 6 ml of pyridine. Stirring was continued for 1 h. The precipitate formed was separated by suction-filtering, washed with acetone and water, and dried. The product was purified by preparative column-chromatography under pressure on silicagel as the adsorbent and by means of a mixture of methylene chloride/ethyl acetate (90/10 by volume) as an eluent.

Yield: 28 g.

Melting point: 114° C.

The quinonoid compounds used in a photographic material of the present invention have as such no reducing properties and must be reduced image-wise to obtain the capability of releasing image-wise a photographically useful substance in alkaline conditions. Such brings about the advantage of a considerably less fog production on storage and development compared with the use of photographic materials initially containing analogous compounds in reduced form as described in the Belgian Pat. No. 861,241 filed Nov. 28, 1977 by Agfa-Gevaert N.V.

A photographic material according to the present invention comprises in its simplest form a support carrying at least one unexposed alkali-permeable silver halide hydrophilic colloid emulsion layer which contains in operative contact therewith or therein a said quinonoid compound that is immobile in an alkali-permeable colloid medium and that contains a photographically useful group and a ballast group, wherein said compound is capable of being reduced by a silver halide developing agent at a rate slower than that of image-wise developable silver halide in the photographic material and in reduced state is capable of releasing said photographically useful group under alkaline conditions.

The quinonoid compounds for use according to the invention are incorporated in the coating liquid for the layers of a photographic material by one of the usual methods. The quantity of such compound used per liter of coating liquid varies within relatively wide limits e.g. dependent on the photographically useful group that is to be split off and the most suitable concentration can be found with the aid of simple tests. For example, from 0.1 to 1 g, preferably from 0.2 to 0.5 g, of quinonoid compound may be used per sq.m. The incorporation into the coating liquid e.g. the silver halide emulsion may proceed, from a dispersion prepared in a sand-mill or by using ultrasound.

According to another method, it may be desired to incorporate the quinonoid compounds in the layer in the form of so-called micro-capsules together with silver halide and optionally also developer substances. In that case, two or more differently sensitized light-sensitive silver halide emulsions and the appropriate diffusion resistant compounds may be combined in a single layer in the form of so-called mixed grain emulsions, for example as described in U.S. Pat. No. 2,698,794 of Leopold Godowsky, issued Jan. 4, 1955. Methods of incorporation in which a quinonoid compound is incorporated into a hydrophilic binder from an alkaline aqueous solution may be applied too since there is no danger of premature hydrolysis of the compound in the quinone form.

According to a preferred embodiment the photographic material contains (a) negative-working silver halide emulsion layer(s) and is capable of providing with said negative-working silver halide emulsion layer(s) positive colour images by using therein said quinonoid compounds that in reduced state and under alkaline conditions are capable of releasing a dye, a dye precursor or a colour coupler.

In a particular embodiment said quinonoid compound is present in a hydrophilic colloid layer adjacent to a silver halide emulsion layer, this adjacent layer being preferably situated behind, viewed in the direction of incident light during exposure, the silver halide emulsion layer.

In an embodiment for producing multicolour images this invention relates to photographic materials that comprise a support carrying (1) a red-sensitive silver halide emulsion layer having operatively associated therewith a said quinonoid compound that is initially immobile in an alkali-permeable colloid medium and wherefrom through the reducing action of a silver halide developing agent and alkalinity a cyan dye is split off in diffusible state, (2) a green-sensitive silver halide emulsion layer having operatively associated therewith said compound of (1) with the difference that a magenta dye is split off in diffusible state, and (3) a blue-sensitive silver halide emulsion layer having operatively associated therewith said compound of (1) with the difference that a yellow dye is split off in diffusible state.

The image dye-providing moiety may be a preformed dye or a shifted dye. Dye materials of this type are well-known in the art and include azo dyes, azomethine (imine) dyes, anthraquinone dyes, alizarine dyes, merocyanine dyes, quinoline dyes, cyanine dyes and the like. The shifted dyes include those compounds whose light-absorption characteristics are shifted hypsochromically or bathochromically when subjected to a different environment such as a change in pH, a reaction with a material to form a complex, a tautomerization, reactions to change the pKa of the compound, a removal of a group such as a hydrolyzable acyl group connected to an atom of the chromophore as mentioned in Weyerts, U.S. Pat. No. 3,260,597 of Stanley R. Scales and Allen E. Wisler, issued July 12, 1966, and the like. In certain embodiments, the shifted dyes are highly preferred, especially those containing a hydrolyzable group on an atom affecting the chromophore resonance structure, since the compounds can be incorporated directly in a silver halide emulsion layer or even on the exposure side thereof without substantial reduction in the light that is effective in the exposure of the silver halide. After exposure, the dye can be shifted to the appropriate colour such as, e.g., by hydrolytic removal of an acyl group to provide the respective image dye.

In another embodiment the compounds of this invention contain an image dye-providing moiety, which is an image-dye precursor. The term "image-dye precursor" is understood to refer to those compounds that undergo reactions encountered in a photographic imaging system to produce an image dye such as colour couplers, oxichromic compounds, and the like.

When colour couplers are used, they can be released in areas where no development occurs and can diffuse to an adjacent layer where they can be made to react with an oxidized colour developer such as an oxidized primary aromatic amine to form the image dye. Generally, the colour coupler and the colour developer are chosen so that the reaction product is immobile. Typical useful colour couplers include the pyrazolone couplers, pyrazolotriazole couplers, open-chain ketomethylene couplers, phenolic couplers and the like. Further reference to the description of appropriate couplers is found in U.S. Pat. No. 3,620,747 of John C. Marchant and Robert F. Motter, issued Nov. 16, 1971, which is incorporated herein by reference.

The compounds containing oxichromic moieties can be advantageously used in a photographic system since they are generally colourless materials due to the absence of an image-dye chromophore. Thus, they can be used directly in the photographic emulsion or on the exposure side thereof without competitive absorption. Compounds of this type are those compounds that undergo chromogenic oxidation to form the respective image dye. The oxidation can be carried out by aerial oxidation, incorporation of oxidants into the photographic element or film unit, or use of an oxidant during processing. Compounds of this type have been referred to in the art as leuco compounds, i.e., compounds that have no colour. Typical useful oxichromic compounds include leuco indoanilines, leuco indophenols, leuco anthraquinones and the like.

Compounds according to the present general formulae have particular application in a diffusion transfer process where it is desired to have a dye or dye precursor entity transferred to an adjacent layer or a receiving element. However, in certain embodiments this invention relates to the release of an image-wise distribution of a diffusible photographically useful compound, which is not a dye or dye precursor but a photographic reagent. Typical useful photographic reagents are known in the art, such as in U.S. Pat. No. 3,227,551 of Charles R. Barr, John Williams and Keith Whitmore, issued Jan. 4, 1966; U.S. Pat. No. 3,364,022 of Charles R. Barr, issued Jan. 16, 1968; U.S. Pat. No. 3,379,529 of Ralph Frederik Porter, Judith A. Schwan and John W. Gates, issued Apr. 23, 1968 and U.S. Pat. No. 3,698,898 of J. Michael Grasshoff and Lloyd D. Taylor, issued Oct. 17, 1972, e.g. a silver-complexing agent acting as a silver halide solvent, a fixing agent, a toning agent, a hardener, an antifogging agent, a sensitizer, a desensitizer, a developer, an oxidizing agent, a development inhibitor or restrainer.

The silver halide development inhibitor includes e.g. triazoles and tetrazoles such as a 5-mercapto-1-phenyl-tetrazole, a 5-methylbenzotriazole, a 4,5-dichlorobenzotriazole and the like. The antifoggant includes e.g. azaindenes such as a tetrazaindene and the like. The compounds that contain releasable silver halide development inhibitors or antifoggants can generally be used in the photographic elements in association with silver halide layers wherein said compound can be incorporated in amounts such as 11 to 1080 mg/sq.m dissolved in a coupler solvent such as diethyl lauramide. When these compounds are incorporated in photographic elements in association with negative silver halide emulsions, a positive image-wise distribution of inhibitor or antifoggant will be produced upon development. Thus, silver development is inhibited or restrained in the low-exposure toe as seen on the H and D curve, but not in the more fully exposed shoulder as also appears from that curve. Development inhibition of the unexposed areas is achieved thereby selectively. When the silver halide emulsions also have dye releasers in accordance with this invention associated therewith, the overall effect of the inhibitor or antifoggant is to release more dye in the unexposed regions, improving maximum image-dye density in the image-receiving layer without increasing the amount of dye released in the exposed regions.

The photographically useful group can also be a silver halide development accelerator such as a benzyl alcohol, a benzyl α-picolinium bromide and the like, a foggant including hydrazines and hydrazides such as an acetylphenylhydrazine and the like, or an auxiliary developer such as a hydroquinone, a 1-phenyl-3-pyrazolidinone, ascorbic acid and the like.

In a specific embodiment in accordance with this invention a photographic material being a film unit is provided that is adapted to be processed by passing said unit between a pair of juxtaposed pressure-applying members, such as would be found in a camera designed for incamera processing. The unit comprises (1) a photosensitive element, which contains a silver halide emulsion layer having associated therewith a said quinonoid compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit such as a rupturable container, which is adapted to be positioned during processing of the film so that a compressive force applied to the container by the pressure-applying members will effect a discharge of the container's contents within the film, and (4) a silver halide developing agent, which is soluble in the alkaline processing composition located within said film unit.

The photographic material of the present invention is useful in a new process comprising (1) applying an alkaline processing composition to the image-wise exposed photographic material comprising a support carrying at least one silver halide emulsion layer and at least one alkali-permeable layer (which may be the same layer as the one containing the silver halide) comprising said quinonoid compound that is initially immobile in an alkaline-permeable colloid medium, wherein said compound is capable of being reduced by a silver halide developing agent at a rate slower than that of image-wise developable silver halide in the material and in reduced state is capable under alkaline conditions of releasing a photographically useful group, (2) providing said developing agent for said photographic material during application of said alkaline processing composition under conditions to effect image-wise release of said photographically useful group inversely proportionally to the image-wise development of said silver halide in the photographic material, and (3) allowing the diffusion with said alkaline processing composition of the photographically useful group out of the layer in which it was originally incorporated to have it introduced image-wise in another layer.

In an embodiment for producing dye images, this invention relates to a photographic colour diffusion transfer process comprising:

(a) treating a photographic element in accordance with this invention with an alkaline processing composition in the presence of a silver halide developing agent to effect development of each of the exposed silver halide emulsion layers, thereby image-wise oxidizing the developing agent and as an inverse function of image-wise silver halide development reducing said immobile quinonoid compound(s) that in reduced state are capable of releasing (a) dye(s);

(b) maintaining said photographic material in the alkaline medium of the processing composition for a time sufficient to release said dye(s) in diffusible state from the reduced immobile compound(s); and (c) transferring at least a portion of said dye(s) to a non-light-sensitive layer acting as a receptor layer.

For in-camera processing the photosensitive material is preferably composed such that the photosensitive silver halide emulsion layer(s) is (are) negative-working and applied to the same support as the receptor layer so as to form an integral combination of light-sensitive layer(s) and a non light-sensitive layer receiver element preferably with an opaque layer, which is alkali-permeable, reflective to light and located between the receptor layer and the silver halide emulsion layer(s). In a process using such material the alkaline processing composition may be applied between the outer photosensitive layer of the photographic element and a cover sheet, which may be transparent and superposed before exposure.

In a modified embodiment, the dye-releasing compound can be incorporated into an alkali-permeable binder of a layer coated on a support other than the support of the silver halide emulsion layer(s) forming a receptor material separate from the light-sensitive material. Said receptor material can be processed by positioning it in interfacial contact with an image-wise exposed photographic silver halide material in the presence of an alkaline solution and a silver halide developing agent. In those areas where unoxidized silver halide developing agent reduces the initially immobile quinonoid compound capable of releasing a dye in alkaline medium when put in reduced state, a pattern of diffusible dye is formed. The diffusible dye is thereupon washed away leaving a reversed pattern of immobile dye in the receptor material. Likewise, if the initially immobile compound contains a tanning agent as the photographically useful moiety, it is possible to obtain a tanned image record in a receptor material in areas corresponding with those of the light-sensitive material where silver halide development does not take place, i.e. a positive tanned image record if a negative-working emulsion is used.

The photographic silver halide materials according to the present invention are processed in the presence of (a) silver halide developing agent(s) that has (have) sufficient reducing power to convert oxidized nucleophilic groups such as oxidized hydroxyl groups on an aromatic nucleus from O= groups into hydroxyl groups again but at a rate slower than that of its (their) own oxidation by image-wise developable silver halide, e.g. of a negative-working silver halide emulsion layer so that image differentiation by image-wise release of a photographically useful compound is still possible.

Photographic silver halide developing agents suitable for that purpose can be found by simple tests using them in combination with an elected set of silver halide and the defined immobile reducible quinonoid compounds that can release in reduced state a photographically useful group under alkaline conditions.

Typical useful silver halide developing agents applicable in the present invention include: hydroquinone compounds, 1-arylpyrazolidin-3-one compounds, pyrogallol and substituted pyrogallol compounds and ascorbic acid or mixtures thereof. These developing agents of which useful representatives are disclosed in the U.S. Pat. No. 3,980,479 are preferably used in non-diffusible state when being with the compounds capable of releasing a photographically useful moiety in admixture in the same colloid layer, e.g. silver halide emulsion layer. Such non-diffusible developing agent is e.g. ascorbyl palmitate.

In a photographic element according to the invention and containing two or more silver halide emulsion layers, each silver halide emulsion layer containing a dye image-providing material or having the dye image-providing material present in a contiguous layer may be separated from the other silver halide emulsion layer(s) in the film unit by (an) interlayer(s), including e.g. gelatin, calcium alginate, or any of the colloids disclosed in U.S. Pat. No. 3,384,483 of Richard W. Becker, issued May 21, 1968, polymeric materials such as polyvinylamides as disclosed in U.S. Pat. No. 3,421,892 of Lloyd D. Taylor, issued Jan. 14, 1969, or any of those disclosed in French Pat. No. 2,028,236 filed Jan. 13, 1970 by Polaroid Corporation or U.S. Pat. Nos. 2,992,104 of Howard C. Haas, issued July 11, 1961 and 3,427,158 of David P. Carlson and Jerome L. Reid, issued Feb. 11, 1969.

According to an embodiment in the preparation of a multicolour diffusion transfer material according to the present invention, a water-permeable colloid interlayer dyed with a yellow non-diffusing dye or Carey Lea silver is applied below the blue-sensitive silver halide emulsion layer containing a yellow dye-releasing compound.

In certain embodiments of our invention and especially with integral format film units, an opacifying agent can be applied from a processing composition. Examples of opacifying agents include carbon black, barium sulphate, zinc oxide, barium stearate, silicates, alumina, zirconium oxide, zirconium acetyl acetate, sodium zirconium sulphate, kaolin, mica, titanium dioxide, organic dyes such as indicator dyes, nigrosines, or mixtures thereof in widely varying amounts depending upon the degree of opacity desired. In general, the concentration of opacifying agent should be sufficient to prevent further exposure of the film units silver halide emulsion or emulsions by ambient actinic radiation through the layer of processing composition, either by direct exposure through a support or by light piping from the edge of the element. For example, carbon black or titanium dioxide will generally provide sufficient opacity when they are present in the processing solution in an amount of from about 5 to 40% by weight. After the processing solution and opacifying agent have been distributed into the film unit, processing may take place out of the camera in the presence of actinic radiation in view of the fact that the silver halide emulsion(s) of the laminate is (are) appropriately protected against incident radiation, at one major surface by the opaque processing composition and at the remaining major surface by the opaque layer that is permeable to alkaline solutions. In certain embodiments, ballasted indicator dyes or dye precursors can be incorporated in a layer on the exposure side of the photosensitive layers; the indicator dye is preferably transparent during exposure and becomes opaque when contacted with the processing composition. Opaque binding tapes can also be used to prevent edge leakage of actinic radiation incident on the silver halide emulsion.

When titanium dioxide or other white pigments are employed as the opacifying agent in the processing composition, it may also be desirable to employ in cooperative relationship therewith a pH-sensitive opacifying dye such as a phthalein dye. Such dyes are light-absorbing or coloured at the pH at which image formation is effected and colourless or not light-absorbing at a lower pH. Other details concerning these opacifying dyes are described in French Specification No. 2,026,927 filed Dec. 22, 1969 by Polaroid Corporation.

The substantially opaque, light-reflective layer, which is permeable to alkaline solutions, in the integral receiver film units of the present invention can generally comprise any opacifier dispersed in a binder as long as it has the desired properties. Particularly desirable are white light-reflective layers since they would be esthetically pleasing backgrounds on which to view a transferred dye image and would also possess the optical properties desired for reflection of incident radiation. Suitable opacifying agents include, as already mentioned with respect to the processing composition, titanium dioxide, barium sulphate, zinc oxide, barium stearate, silver flake, silicates, alumina, zirconium oxide, zirconium acetyl acetate, sodium zirconium sulphate, kaolin, mica, or mixtures thereof in widely varying amounts depending upon the degree of opacity desired. The opacifying agents may be dispersed in any binder such as an alkaline solution-permeable polymer matrix such as, for example, gelatin, polyvinyl alcohol, and the like. Brightening agents such as the stilbenes, coumarins, triazines and oxazoles may also be added to the light-reflective layer, if desired. When it is desired to increase the opacifying capacity of the light-reflective layer, dark-coloured opacifying agents may be added to it, e.g., carbon black, nigrosine dyes, etc. Another technique to increase the opacifying capacity of the light-reflective layer is to employ a separate opaque layer underneath it comprising, e.g., carbon black, nigrosine dyes, etc., dispersed in a polymeric matrix that is permeable to alkaline solutions such as, e.g., gelatin, polyvinyl alcohol, and the like. Such an opaque layer would generally have a density of at least 4 and preferably greater than 7 and would be substantially opaque to actinic radiation. The opaque layer may also be combined with a developer scavenger layer if one is present. The light-reflective and opaque layers are generally 0.025 to 0.15 mm in thickness, although they can be varied depending upon the opacifying agent employed, the degree of opacity desired, etc.

The photosensitive substances used in this invention are preferably silver halide compositions and may comprise silver chloride, silver bromide, silver bromoiodide, silver chlorobromoiodide and the like, or mixtures thereof. The emulsions may be coarse- or fine-grain and can be prepared by any of the well-known procedures, e.g., single-jet emulsions, double-jet emulsions, such as Lippmann emulsions, ammoniacal emulsions, thiocyanate- or thioether-ripened emulsions such as those described in U.S. Pat. No. 2,222,264 of Adolph H. Nietz and Frederick J. Russell, issued Nov. 19, 1940, U.S. Pat. No. 3,320,069 of Bernard D. Illingsworth, issued May 16, 1967, and 3,271,157 of Clarence E. McBride, issued Sept. 6, 1966. Surface-image emulsions may be used or internal-image emulsions may be used such as those described in U.S. Pat. No. 2,592,250 of Edward Philip Davey and Edward Bowes Knott, issued Apr. 8, 1952, 3,206,313 of Henry D. Porter, Thomas H. James and Wesley G. Lowe, issued Sept. 14, 1965, and U.S. Pat. No. 3,447,927 of Robert E. Bacon and Jean F. Barbier, issued June 3, 1969. The emulsions may be regular-grain emulsions such as the type described by Klein and Moisar in J. Photogr. Sci., Vol. 12, No. 5, September/October, 1964, pp. 242-251. If desired, mixtures of surface- and internal-image emulsions may be used as described in U.S. Pat. No. 2,996,382 of George W. Luckey and John C. Hoppe, issued Aug. 15, 1961.

Negative-type or direct-positive emulsions may be used such as those described in U.S. Pat. No. 2,184,013 of John A. Leermakers, issued Dec. 19, 1939, U.S. Pat. No. 2,541,472 of William B. Kendall and George D. Hill, issued Feb. 13, 1951, U.S. Pat. No. 3,367,778 of Robert W. Berriman, issued Feb. 6, 1968, U.S. Pat. No. 3,501,307 of Bernard D. Illingsworth, issued Mar. 17, 1970, U.S. Pat. No. 2,563,785 of Charles F. Ives, issued Aug. 7, 1951, U.S. Pat. No. 2,456,953 of Edward Bowes Knott and Guy William Willis, issued Dec. 21, 1948, U.S. Pat. No. 2,861,885 of Edwin H. Land, issued Nov. 25, 1958, U.S. Pat. No. 3,761,276 of Francis John Evans, issued Sept. 25, 1973, U.S. Pat. No. 3,761,266 of Kirby Mitchell Milton, issued Sept. 25, 1973, U.S. Pat. No. 3,736,140 of Susan Starr Collier and Paul Brewster Gilman Jr., issued May 29, 1973, and U.S. Pat. No. 3,730,723 of Paul Brewster Gilman Jr., Ronald George Raleigh and Thaddeus Donald Koszelak, issued May 1, 1973, and United Kingdom Patent Specification No. 723,019 filed Feb. 5, 1952 by Gevaert Photo-Producten N.V.

Silver halide emulsions useful in our invention are well-known to those skilled in the art. More details about their composition, preparation and coating are described, e.g., in Product Licensing Index, Vol. 92, December 1971, publication 9232, p. 107-109.

According to one embodiment, the silver halide emulsion layers in the invention comprise photosensitive silver halide dispersed in gelatin and are about 0.2 to 2 $\mu$m thick; the dye image-providing materials are dispersed in a polymeric binder permeable to alkaline solutions, such as gelatin, to form a separate layer of about 1 to 7 $\mu$m thick, in combination with polymeric interlayers permeable to alkaline solutions, e.g., gelatin, being about 1 to 5 $\mu$m thick. Of course, these thicknesses are approximate only and may be modified according to the product desired.

The support for the photographic elements of this invention may be any material as long as it does not deleteriously affect the photographic properties of the film unit and is dimensionally stable. Typical flexible sheet materials are paper supports, e.g. coated at one or both sides with an $\alpha$-olefin polymer, e.g. polyethylene; they include cellulose nitrate film, cellulose acetate film, poly(vinyl acetal) film, polystyrene film, poly(ethylene terephthalate) film, polycarbonate film, poly-$\alpha$-olefins such as polyethylene and polypropylene film, and related films or resinous materials. The support is usually about 0.05 to 0.15 mm thick. For use in colour photography any material can be employed as the image-receiving layer as long as the desired function of mordanting or otherwise fixing the diffused dye will be obtained. The particular material chosen will, of course, depend upon the dye to be mordanted. If acid dyes are to be mordanted, the image-receiving layer can be composed of or contain basic polymeric mordants such as polymers of amino-guanidine derivatives of vinyl methyl ketone such as described in U.S. Pat. No. 2,882,156 of Louis M. Minsk, issued Apr. 14, 1959, and basic polymeric mordants and derivatives, e.g. poly-4-vinylpyridine, the 2-vinylpyridine polymer metho-p-toluene sulphonate and similar compounds described in U.S. Pat. No. 2,484,430 of Robert H. Sprague and Leslie G. Brooker, issued Oct. 11, 1949, the compounds described in the published German Patent Application No. 2,200,063 filed Jan. 11, 1971 by Agfa-Gevaert A. G. Suitable mordanting binders include, e.g. guanylhydrazone derivatives of acyl styrene polymers, as described e.g. in published German Patent Specification No. 2,009,498 filed Feb. 28, 1970 by Agfa-Gevaert A. G. In general, however, other binders, e.g. gelatin, would be added to the last-mentioned mordanting binders. Effective mordanting compositions are long-chain quaternary ammonium or phosphonium compounds or ternary sulphonium compounds, e.g. those described in U.S. Pat. No. 3,271,147 of Walter M. Bush and U.S. Pat. No. 3,271,148 of Keith E. Whitmore, both issued Sept. 6, 1966, and cetyltrimethyl-ammonium bromide. Certain metal salts and their hydroxides that form sparingly soluble compounds with the acid dyes may be used too. The dye mordants are dispersed in one of the usual hydrophilic binders in the image-receiving layer, e.g. in gelatin, polyvinylpyrrolidone or partly or completely hydrolysed cellulose esters.

Generally, good results are obtained when the image-receiving layer, which is preferably permeable to alkaline solution, is transparent and about 4 to about 10 μm thick. This thickness, of course, can be modified depending upon the result desired. The image-receiving layer may also contain ultraviolet-absorbing materials to protect the mordanted dye images from fading, brightening agents such as the stilbenes, coumarins, triazines, oxazoles, dye stabilizers such as the chromanols, alkyl-phenols, etc.

Use of pH-lowering material in the dye-image-receiving element of a film unit according to the invention will usually increase the stability of the transferred image. Generally, the pH-lowering material will effect a reduction of the pH of the image layer from about 13 or 14 to at least 11 and preferably 5–8 within a short time after imbibition. For example, polymeric acids as disclosed in U.S. Pat. No. 3,362,819 of Edwin H. Land, issued Jan. 9, 1968 or solid acids or metallic salts, e.g. zinc acetate, zinc sulphate, magnesium acetate, etc., as disclosed in U.S. Pat. No. 2,584,030 of Edwin H. Land, issued Jan. 29, 1952, may be employed with good results. Such pH-lowering materials reduce the pH of the film unit after development to terminate development and substantially reduce further dye transfer and thus stabilize the dye image.

An inert timing or spacer layer may be employed in practice over the pH-lowering layer, which "times" or controls the pH reduction depending on the rate at which alkali diffuses through the inert spacer layer. Examples of such timing layers include gelatin, polyvinyl alcohol or any of the colloids disclosed in U.S. Pat. No. 3,455,686 of Leonard C. Farney, Howard G. Rogers and Richard W. Young, issued July 15, 1969. The timing layer may be effective in evening out the various reaction rates over a wide range of temperatures, e.g., premature pH reduction is prevented when inbibition is effected at temperatures above room temperature, e.g. at 35° to 37° C. The timing layer is usually about 2.5 μm to about 18 μm thick. Especially good results are obtained when the timing layer comprises a hydrolysable polymer or a mixture of such polymers that are slowly hydrolysed by the processing composition. Examples of such hydrolysable polymers include polyvinyl acetate, polyamides, cellulose esters, etc.

An alkaline processing composition employed in this invention can be a conventional aqueous solution of an alkaline material, e.g. sodium hydroxide, sodium carbonate or an amine such as diethylamine, preferably possessing a pH beyond 11.

According to one embodiment the alkaline processing liquid contains the diffusible developing agent that effects the reduction of the silver halide, e.g. ascorbic acid or a 3-pyrazolidinone developing agent such as 1-phenyl-4-methyl-3-pyrazolidinone.

The alkaline processing composition employed in this invention may also contain a desensitizing agent such as methylene blue, nitro-substituted heterocyclic compounds, 4,4'-bipyridinium salts, etc., to insure that the photosensitive element is not further exposed after it is removed from the camera for processing.

The solution also preferably contains a viscosity-increasing compound such as a high-molecular-weight polymer, e.g. a water-soluble ether inert to alkaline solutions such as hydroxyethylcellulose or alkali metal salts of carboxymethylcellulose such as sodium carboxymethylcellulose. A concentration of viscosity-increasing compound of about 1 to about 5% by weight of the processing composition is preferred. It will impart thereto a viscosity of about 100 mPa.s to about 200,000 mPa.s.

Processing may proceed in a tray developing unit as is present, e.g., in an ordinary silver complex diffusion transfer (DTR) apparatus in which the contacting with a separate dye image-receiving material is effected after a sufficient absorption of processing liquid by the photographic material has taken place. A suitable apparatus for said purpose is the COPYPROOF CP 38 (trade name) DTR-developing apparatus. COPYPROOF is a trade name of Agfa-Gevaert, Antwerpen/Leverkusen.

According to other embodiments wherein the receptor layer is integral with the photosensitive layer(s) the processing liquid is applied from a rupturable container or by spraying.

The rupturable container that may be employed in this invention may be of the type disclosed in U.S. Pat. No. 2,543,181 of Edwin H. Land, issued Feb. 27, 1951, U.S. Pat. No. 2,643,886 of Ulrich L. di Ghilini, issued June 30, 1953, U.S. Pat. No. 2,653,732 of Edwin H. Land, issued Sept. 29, 1953, U.S. Pat. No. 2,723,051 of William J. McCune Jr., issued Nov. 8, 1955, U.S. Pat. Nos. 3,056,492 and 3,056,491, both of John E. Campbell, issued Oct. 2, 1962, and U.S. Pat. No. 3,152,515 of Edwin H. Land, issued Oct. 13, 1964. In general such containers comprise a rectangular sheet of fluid- and air-impervious material folded longitudinally upon itself to form two walls that are sealed to one another along their longitudinal and end margins to form a cavity in which processing solution is contained.

While the alkaline processing composition used in this invention can be employed in a rupturable container, as described previously, to facilitate conveniently the introduction of processing composition into the film unit, other means of discharging processing composition within the film unit could also be employed, e.g., means injecting processing solution with communicating members similar to hypodermic syringes, which are attached either to a camera cartridge, as described in U.S. Pat. No. 3,352,674 of Donald M. Harvey, issued Nov. 14, 1967.

The main aspect of the present invention is the use of quinonoid compounds from which by reduction and in alkaline medium a dye is released as photographically useful fragment. This is the reason why, in the following, mainly reference is made to colour providing compounds. The invention, however, is not at all limited to this aspect and it should be kept in mind that for various other purposes other photographically useful fragments may be present in these compounds instead of dyes or dye precursors.

The following examples further illustrate the invention. All percentages and ratios are by weight, unless otherwise mentioned.

EXAMPLE 1

Comparative embodiment A

A subbed water-resistant paper support consisting of a paper sheet of 110 g/sq.m coated at both sides with a polyethylene stratum of 15 g/sq.m was treated with a corona discharge and thereupon coated in the mentioned order with the following layers, the amounts relating to 1 sq.m of material:

---

(1) an alkali-permeable colloid layer containing after drying per sq.m:

| | |
|---|---|
| gelatin | 2.198 g |
| cyan dye-providing quinonoid compound C1 (applied from a dispersion prepared as described hereinafter) | 0.253 g (0.232 millimole) |
| silver chloride (applied from a gelatin-silver chloride emulsion) | 1.207 g (7 millimole) |
| ascorbyl palmitate (applied from a dispersion prepared as described hereinafter) | 0.497 g (1.2 millimole) |
| (2) anti-stress layer containing per sq.m: | |
| gelatin | 2 g |
| 1-phenyl-3-pyrazolidinone (applied from a dispersion prepared as described hereinafter) | 0.165 g |

Processing

A sheet of the obtained photographic material was exposed through a grey wedge having a constant 0.1 and thereupon contacted with the receptor material described hereinafter in the COPYPROOF CP 38 (trade name) diffusion transfer processing apparatus containing in its tray an aqueous solution comprising per liter:

| | |
|---|---|
| sodium hydroxide | 7 g |
| sodium orthophosphate | 25 g |
| N-methyl-pyrrolidinone | 80 ml |
| 1% ethanolic solution of 1-phenyl-2-tetrazoline-5-thione | 20 ml |
| potassium bromide | 5 g |
| distilled water up to | 1000 ml |

After a contact time of 1 min the receptor material and light-sensitive material were peeled apart and dried.

Composition of the receptor material

To the same support as described for the above light-sensitive material a coating having the following composition was applied per sq.m:
gelatin 5 g
triphenyl-n-hexadecylphosphonium bromide 2 g

Preparation of the dispersion of cyan dye-providing compound C1

The preparation proceeded by sand-milling and using the following ingredients:

| | |
|---|---|
| compound C1 (prepared as described after Table 2 hereinafter) | 5 g |
| distilled water | 81.5 ml |
| gelatin | 5 g |
| 40% aqueous solution of the wetting agent LOMAR D (trade name) | 3 ml |
| isopropanol | 5 ml |
| sodium acetate | 0.5 g |

(LOMAR D is a trade name of Nopco Chemical Company, Newark, N.J., U.S.A. for a naphthalene sulphonate condensate, formaldehyde being used in the condensation reaction).

Preparation of the dispersion of ascorbyl palmitate having the following structural formula:

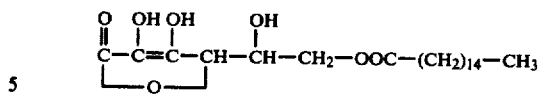

50 g of ascorbyl palmitate were first dissolved in 450 ml of ethanol forming solution A.

A solution of 125 g of gelatin in 1975 ml of distilled water was prepared and added to a solution containing 4.8 g of sodium hydroxide, 0.2 ml of n-octylalcohol and 95 ml of distilled water forming that way solution B. Thereupon solution A was thoroughly mixed with solution B.

Preparation of the dispersion of 1-phenyl-3-pyrazolidinone.

The preparation proceeded by sand-milling with the following ingredients:

| | |
|---|---|
| gelatin | 40 g |
| 1-phenyl-3-pyrazolidinone | 100 g |
| 40% aqueous solution of LOMAR D (trade name) | 10 ml |
| distilled water | 850 ml |

Comparative embodiment B

Comparative embodiment A was repeated with the difference, however, that instead of compound C1 the cyan dye-providing compound I of Table 1 was used.

The dispersion of said compound I was prepared with the following ingredients:

| | |
|---|---|
| compound I | 6 g |
| distilled water | 573 ml |
| gelatin | 15 g |
| 10% aqueous solution of MARLON A-396 (trade name) | 6 ml |

Compound I was first dissolved in ethyl acetate and added whilst vigorous stirring to the gelatin dissolved in the indicated amount of water. Thereupon the ethyl acetate was removed by evaporation under reduced pressure.

(MARLON A-396 is a trade name of Chemische Werke Hüls AG Marl/Westfalen, W. Germany for a wetting agent having the formula:

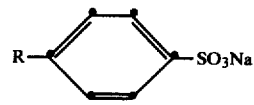

wherein R is $C_{10}$–$C_{13}$ n-alkyl)

Comparative embodiment C

Comparative embodiment A was repeated with the difference, however, that instead of $C_1$ the cyan dye-providing compound II of Table 1 was used.

Comparative embodiment D

Comparative embodiment A was repeated with the difference, however, that instead of compound C1 the cyan dye-providing compound III of Table 1 was used.

Comparative embodiment E

Comparative embodiment A was repeated with the difference, however, that instead of compound C1 the cyan dye-providing compound IV of Table 1 was used.

The dispersion of said compound IV was prepared by sand-milling the following ingredients:

| | |
|---|---|
| compound IV | 8.5 g |
| distilled water | 174.5 ml |
| gelatin | 8.5 g |
| 40% aqueous solution of LOMAR D (trade name) | 5.1 ml |
| isopropanol | 8.5 ml |
| sodium acetate | 0.85 g |

| | Sensitometric results | |
|---|---|---|
| | Cyan dye density (D) | |
| Comparative embodiment | Dmin (fog) | Dmax |
| A | 0.08 | 0.57 |
| B | 0.17 | 1.70 |
| C | 0.18 | 2.22 |
| D | 0.07 | 1.80 |
| E | 0.11 | 1.08 |

EXAMPLE 2

Comparative embodiment M

A subbed water-resistant paper support consisting of a paper sheet of 110 g/sq.m coated at both sides with a polyethylene stratum of 15 g/sq.m was treated with a corona discharge and thereupon coated in the mentioned order with the following layers, the amounts relating to 1 sq.m of material:

| | | |
|---|---|---|
| (1) an alkali-permeable colloid layer containing after drying per sq.m: | 2.163 g | |
| gelatin | | |
| magenta dye-providing quinonoid compound M1 | 0.339 g | |
| (applied from a dispersion prepared as described hereinafter) | (0.360 millimole) | |
| silver chloride | 1.535 g | |
| (applied from a gelatin-silver chloride emulsion) | (9 millimole) | |
| ascorbyl palmitate | 0.564 g | |
| (applied from a dispersion prepared as described in Example 1) | (1.36 millimole) | |
| (2) anti-stress layer containing per sq.m: | 2 g | |
| gelatin | | |
| 1-phenyl-3-pyrazolidinone | 0.165 g | |
| (applied from a dispersion prepared as described in Example 1) | | |

Processing

The processing proceeded as in Example 1 but with the following composition:

| | |
|---|---|
| sodium hydroxide | 7 g |
| sodium orthophosphate | 25 g |
| N-methylpyrrolidinone | 30 ml |
| 1-phenyl-3-pyrazolidinone | 5 g |
| 1% ethanolic solution of 1-phenyl-2-tetrazoline-5-thione | 20 ml |
| potassium bromide | 5 g |
| distilled water up to | 1000 ml |

Preparation of the dispersion of magenta dye-providing compound M1

The preparation proceeded by sand-milling the following ingredients:

| | |
|---|---|
| compound M1 (prepared as described after Table 2 hereinafter) | 3.8 g |
| distilled water | 186.4 ml |
| gelatin | 3.8 g |
| 40% aqueous solution of LOMAR D (trade name) | 2.28 ml |
| isopropanol | 3.8 ml |
| sodium acetate | 1 g |

Comparative embodiment N

Comparative embodiment M was repeated with the difference, however, that instead of compound M1 the magenta dye-providing compound V of Table 1 was used.

The dispersion of said compound V was prepared with the following ingredients:

| | |
|---|---|
| compound V | 5.5 g |
| distilled water | 525.2 ml |
| gelatin | 13.8 g |
| 10% aqueous solution of MARLON A-396 (trade name) | 5.5 ml |

Compound V was first dissolved in ethyl acetate and added whilst vigorous stirring to the gelatin dissolved in the indicated amount of water. Thereupon the ethyl acetate was removed by evaporation under reduced pressure.

| | Sensitometric results | |
|---|---|---|
| | Magenta dye density (D) | |
| Comparative embodiment | Dmin (fog) | Dmax |
| M | 0.06 | 0.30 |
| N | 0.08 | 1.66 |

EXAMPLE 3

Comparative embodiment Y

A subbed water-resistant paper support consisting of a paper sheet of 110 g/sq.m coated at both sides with a polyethylene stratum of 15 g/sq.m was treated with a corona discharge and thereupon coated in the mentioned order with the following layers, the amounts relating to 1 sq.m of material:

| | | |
|---|---|---|
| (1) an alkali-permeable colloid layer containing after drying per sq.m | | |
| gelatin | 1.448 g | |
| Yellow dye-providing quinonoid compound Y1 | 0.395 g | |
| (applied from a dispersion prepared as described hereinafter) | (0.446 millimole) | |
| silver chloride | 1.207 g | |
| (applied from a gelatin silver chloride emulsion) | (7 millimole) | |
| ascorbyl palmitate | 0.497 g | |
| (applied from a dispersion prepared as described hereinafter) | (1.2 millimole) | |
| (2) anti-stress layer containing per sq.m: | | |
| gelatin | 2 g | |
| 1-phenyl-3-pyrazolidinone | 0.165 g | |
| (applied from a dispersion prepared | | |

-continued

| as described hereinafter) |
|---|

Processing

The processing proceeded as in Example 1.
Preparation of the dispersion of yellow dye-providing compound Y1.
The dispersion of compound Y1 was prepared with the following ingredients:

-continued

| isopropanol | 6.4 ml |
|---|---|
| sodium acetate | 0.64 ml |

| | Sensitometric results | |
|---|---|---|
| | Yellow dye density (D) | |
| Comparative embodiment | Dmin (fog) | Dmax |
| Y | 0.08 | 0.48 |
| X invention VII | 0.08 | 0.60 |

TABLE 2

| Compound | Structural formula |
|---|---|
| C1 | (structure shown) |
| M1 | (structure shown) |
| Y1 | (structure shown) |

| compound Y1 | 5 g |
|---|---|
| distilled water | 477.5 ml |
| gelatin | 12.5 g |
| 10% aqueous solution of MARLON A-396 (trade name) | 5 ml |

Compound Y1 was first dissolved in ethyl acetate and added whilst vigorous stirring to the gelatin dissolved in the indicated amount of water. Thereupon the ethyl acetate was removed by evaporation under reduced pressure.

Comparative embodiment X

Comparative embodiment X was repeated with the difference, however, that instead of compound Y1 the yellow dye-providing compound VII of Table 1 was used.

The dispersion of said compound VII was prepared by sand-milling the following ingredients:

| compound VII | 6.4 g |
|---|---|
| distilled water | 252 ml |
| gelatin | 6.4 g |
| 40% aqueous solution of LOMAR D (trade name) | 4 ml |

The above comparative compounds are of the type described in published European Patent Application 0,004,399 and can be prepared as follows.

Preparation compound C1

(a) 2,3-Dimethyl-6-myristoyl-hydroquinone 93 g of 2,3-dimethyl-hydroquinone and 168 g of myristic acid were dissolved with stirring in 300 ml of 1,2-dichloroethane and heated to 80° C. Boron trifluoride was bubbled through for 4 h and stirring was continued at 80° C. for 2 h. The reaction mixture was poured into 1800 ml of water containing 200 g of dissolved sodium acetate. The organic layer was separated, washed with water and the solvent evaporated in a rotary evaporator. Any precipitate formed during washing should be filtered off and be recrystallized together with the residue after evaporation. The crystallization was effected from a mixture of 1,2-dichloroethane and benzine (1:1 by volume). Yield: 126 g. Melting point: 100° C.

(b) 2,3-Dimethyl-4-allyloxy-6-myristoyl-phenol 418 g of compound C1a were dissolved in 4.8 l of methyl ethyl ketone to which 252 g of finely pulverized anhydrous potassium carbonate were added. Whilst stirring the mixture was brought to refluxing temperature. Then 165 g of allyl bromide were dropwise added within a period of 2 h. Refluxing was continued for 20 h. Thereupon the reaction mixture was cooled to 30° C. and poured into 800 ml of water. The organic layer was separated and washed with 500 ml of 25% by weight aqueous sodium chloride solution. In a rotary evaporator the solvent was removed and the residue was treated with 4 l of hot methanol. After cooling to 15° C. the precipitate was suction-filtered and dried. Yield: 370 g. Melting point: 65°–66° C.

(c) 2,3-Dimethyl-5-allyl-6-myristoyl-hydroquinone 370 g of compound C1b were heated under nitrogen atmosphere on an oil-bath at 200° C.–210° C. for 1 h.

Thereupon the reaction mass was cooled to 70° C. and 1200 ml of almost boiling benzine were poured on it with stirring. After cooling, the solid product was suction-filtered. Yield: 221 g. Melting point: 68°–69° C.

(d) 2,3-Dimethyl-5-n-propyl-6-myristoyl-hydroquinone

To 221 g of compound C1c sufficient ethanol was added to obtain a liquid volume of 2 l. Thereto Raney-nickel was added as a hydrogenation catalyst. Reduction proceeded at 23° C. under a hydrogen pressure of 28.12 kg/sq.cm for 40 min. The catalyst was filtered off and the solvent of the filtrate removed in a rotary evaporator. Yield: 216 g. Melting point: 70° C.

(e) 2,3-Dimethyl-5-n-propyl-6-hydroxytetradecylhydroquinone 97.5 g (0.25 mole) of compound C1d were pulverized and dissolved in 2.5 l of methanol under nitrogen atmosphere with stirring. To the obtained solution a solution of 9.5 g (0.25 mole) of sodium borohydride in 125 ml of water was dropwise added with ice-cooling. After the addition, cooling was stopped and stirring under nitrogen atmosphere was continued for 30 min. The end of the reaction was checked by thin-layer chromatography. At the end 80 ml of acetic acid were added dropwise with care. After 10 min the reaction mixture was added dropwise with stirring to 2.5 l of ice-water containing 15 ml of concentrated sulphuric acid. Stirring was continued for 15 min and the precipitate formed was sucked off, washed with water till neutral and dried.

Yield: 99 g. Melting point: 90° C.

(f) Hydroquinone form of compound C1

12 g of compound C1e were dissolved at 60° C. in 600 ml of acetic acid forming solution A.

To solution A the following mixture heated at 60° C. was added: 26 g of compound 5a prepared according to published European patent application No. 0.004.399, 3 g of sodium acetate, 500 ml of acetic acid and 360 ml of water. The obtained reaction mixture was stirred at 75° C. for 45 min. After cooling, the formed precipitate was suction-filtered, washed with a mixture of methanol/water (1:1 by volume) and dried. Yield: 28.3 g.

(g) Compound C1

22.2 g (20 millimole) of compound C1f were stirred at 75° C. in 250 ml of ethylene glycol monomethyl ether. Then 2.5 g (23 millimole) of p-benzoquinone were added and a complete dissolution was obtained.

The reaction mixture was stirred at 75° C. for 30 min and cooled, whereupon 70 ml of water were added. After standing for 12 h the precipitate was suction-filtered, washed with a mixture of methanol/water (1:2 by volume), dried and purified by preparative column-chromatography by means of silica gel adsorbent and methylene chloride/ethyl acetate (95/5 by volume) as the eluent. Yield: 18.3 g.

Preparation of compound M1

(a) Hydroquinone form of compound M1

6 g of compound C1e were dissolved at 60° C. in 300 ml of acetic acid forming solution A.

8.6 g of compound Vc, 1.5 g of sodium acetate, and 250 ml of acetic acid were dissolved in 180 ml of water at 60° C. and thereupon added to solution A. The reaction mixture was heated at 70° C. for 3 h and then cooled. The precipitate formed was suction-filtered and dried. Yield: 5.5 g.

(b) Compound M1

5.5 g of compound M1a were dissolved in 50 ml of ethylene glycol monomethyl ether and 1.5 g of p-benzoquinone were added. The reaction mixture was stirred at 20° C. for 1.5 h. Thereupon it was poured into water acidified with a few drops of hydrochloric acid. The precipitate formed was treated with water and purified with preparative column-chromatography by means of silica gel as an adsorbent and a mixture of methylene chloride/ethyl acetate (90/10 by volume) as an eluent.

Yield: 1.9 g.

Preparation of Compound Y1

(a) 3-methyl-6-myristoyl-hydroquinone 228 g (1 mole) of myristic acid and 136 g (1.1 mole) of monomethylhydroquinone were melted together whilst stirring a 100° C. and saturated with boron trifluoride for 4 h. After being stirred for 2 h at 100° C. the mixture was poured into 3 l of water. The product formed was pulverized under water and neutralized with a solution of 110 g of sodium carbonate in 400 ml of water, suction-filtered, washed with water, dried, and recrystallized from benzine. Yield: 305 g of compound Y1a. Melting point: 83° C.

(b) 3-methyl-4-allyloxy-6-myristoyl-phenol 100 g (0.3 mole) of compound Y1a were dissolved in 1 l of methyl ethyl ketone. Then 61.2 g of pulverized anhydrous potassium carbonate were added. The reaction mixture was stirred and heated to reflux temperature. Then 30 ml (41.4 g) of allyl bromide were slowly added dropwise. The reaction mixture was refluxed for 8 h, cooled and poured into 600 ml of water. The organic layer was separated, washed twice with an aqueous 25% by weight solution of sodium chloride and dried on sodium sulphate. The solvent was removed in a rotary evaporator. The residue was crystallized from methanol. Yield: 72 g. The structure of compound Y1b was confirmed by NMR.

(c) 3-methyl-5-allyl-6-myristoyl-hydroquinone 269 g of compound Y1b were melted at 200°–201° C. under nitrogen atmosphere for 1 h. After cooling, 880 ml of benzine were added. The reaction mixture was stirred and cooling continued to 15° C. The formed precipitate was suction-filtered and washed with benzine. Yield: 221 g. Melting point: 60° C.

(d) 3-methyl-5-n-propyl-6-myristoyl-hydroquinone

To 170.5 g of compound Y1c a sufficient amount of ethanol was added to bring the volume of the mixture to 1.7 l. Raney-nickel was added as a hydrogenation catalyst. Hydrogenation was effected at 20° C. under a hydrogen pressure of 5.6 kg/sq.cm within 20 min. After filtering off the catalyst the organic solvent was removed in a rotary evaporator. The residue was recrystallized from 750 ml of benzine. By cooling to 3° C. 149.6 g of compound Y1d were obtained. Melting point: 62° C. Structure confirmed by NMR.

(e) 3-methyl-5-n-propyl-α-hydroxy-tetradecylhydroquinone 263.2 g (0.7 mole) of compound Y1d were dissolved in 3 l of hot methanol under nitrogen atmosphere. The solution was cooled to 40° C. and a solution of 30.6 g of sodium borohydride in 140 ml of water was added thereto dropwise with stirring while cooling with ice-water was continued. Stirring was continued for 30 min. The end of the reaction was checked with thin-layer chromatography. Then 200 ml of acetic acid were added dropwise. The reaction mixture was poured with stirring into 4 l of ice water to which 40 ml of concentrated sulphuric acid were added. The precipitate was suction-filtered, washed and dried. Yield: 270 g. Melting point: 123° C.

(f) Hydroquinone form of compound Y1

7.6 g (20 millimole) of compound Y1e were dissolved at 50° C. in 150 ml of acetic acid forming solution A. At 50° C. a solution of 20.8 g of compound 1e, prepared according to the published European Patent Application 0,004,399, 2 g of sodium acetate, and 360 ml of acetic acid in 240 ml of water were added to solution A. It was heated to 60° C. for 4 h and to 70° C. for 2 h. The mixture was cooled, the formed precipitate sucked off and washed with a mixture of methanol/water (1:1 by volume) and dried. Yield: 9.5 g.

(g) Compound Y1

9.5 g of compound Y1f were dissolved at 50° C. in 90 ml of ethylene glycol monomethyl ether. Then 2 g of p-benzoquinone were added at 60° C. within a period of 30 min. Thereupon the reaction mixture was cooled, the precipitate formed suction-filtered, washed with a mixture of methanol/water (1:1 by volume), and purified by preparative column-chromatography with silica gel as an adsorbent and a mixture of methylene chloride/ethyl acetate (95:5 by volume) as an eluent. Yield: 5.1 g.

We claim:

1. A photographic silver halide material comprising a support carrying at least one unexposed alkali-permeable silver halide hydrophilic colloid emulsion layer which contains therein a quinonoid compound having a para- or ortho-quinonoid nucleus and which compound is immobile in an alkali-permeable colloid medium when contacted with an alkaline liquid and which contains a photographically useful group and a ballast group, wherein said compound is capable of being reduced by a silver halide developing agent at a rate slower than that of image-wise developable silver halide in the photographic material and in reduced state is capable of releasing said photographically useful group under alkaline conditions, characterized in that said quinonoid compound corresponds to one of the following formulae (A) or (B):

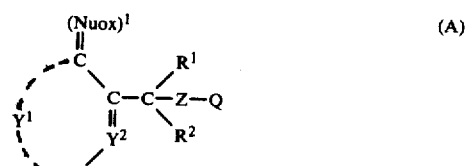

(A)

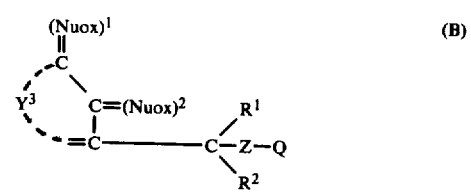

(B)

wherein:

each of (Nuox)$^1$ and (Nuox)$^2$ (same or different) represents an oxidized nucleophilic group, Z represents a bivalent atom or a bivalent atomic group, which is electro-negative with respect to the carbon atom carrying R$^1$ and R$^2$, Q together with the group Z represents a releasable photographically useful group, Y$^1$ and Y$^2$ together represent the necessary atoms to close a p-quinonoid ring substituted with (a) directly linked monovalent organic ring or ring system substituent(s) having aromatic character, Y$^3$ represents the necessary atoms to close an o-quinonoid ring substituted with (a) directly linked monovalent organic ring or ring system substituent(s) having aromatic character, and each of R$^1$ and R$^2$ (same or different) represents hydrogen or a hydrocarbon group, at least R$^1$, R$^2$ or a substituent on the quinonoid ring being or containing a ballasting group X of sufficient size to keep said compound immobile in an alkali-permeable layer of the photographic material when said layer is contacted with an alkaline liquid, the monovalent organic ring or ring system substituent having aromatic character being a monovalent organic substituent derived from an organic substance having only carbon atoms or carbon atoms and (a) heteroatom(s) linked to each other forming a ring or ring system stabilized by resonance due to overlapping π-orbitals of alternating double bonds or of double bonds and (a) lone pair p-orbital(s) of (a) hetero atom(s), whereby the Hückel rule is obeyed, said rule stating that (4n+2) electrons should be present in the overlapping orbitals, n being any positive integer here not including zero.

2. A photographic material according to claim 1, characterized in that the said monovalent organic ring or ring system substituent having aromatic character is present on the quinonoid nucleus in ortho-position to the

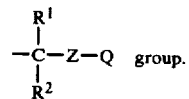

group.

3. A photographic material according to claim 1, characterized in that $Y^1$ and $Y^2$ together represent the necessary atoms to close a p-quinonoid ring substituted with (an) aryl group(s) and $Y^3$ represents the necessary atoms to close an o-quinonoid ring substituted with (an) aryl group(s).

4. A photographic material according to claim 3, characterized in that an aryl substituted on the para- or ortho-quinonoid ring is an alkoxy substituted phenyl group.

5. A photographic material according to claim 1, characterized in that the photographically useful group represents a dye.

6. A photographic material according to claim 1, characterized in that the group $(Nuox)^1$ and the group $(Nuox)^2$ each are $O=$ groups stemming from the oxidation of HO-groups.

7. A photographic material according to claim 1, characterized in that Z represents a bivalent sulphur atom or a sulphonyl group.

8. A photographic material according to claim 1, characterized in that $R^1$ or $R^2$ represents a phenyl group.

9. A photographic material according to claim 1, characterized in that the para- or ortho-quinonoid nucleus is further substituted with one or more other substituents selected from the group of halogen, non-aromatic hydrocarbon, alkoxy, aryloxy, acylamino wherein the acyl group is derived from aliphatic or aromatic carboxylic or sulphonic acids, an amino group, alkylthio, arylthio or sulpho, or wherein the substituted para- or ortho-quinonoid nucleus forms part of a fused ring system.

10. A photographic material according to claim 1, comprising a support carrying (1) a red-sensitive silver halide emulsion layer having operatively associated therewith a said quinonoid compound that is initially immobile in an alkali-permeable colloid medium and wherefrom through the reducing action of a silver halide developing agent and alkalinity a cyan dye is split off in diffusible state, (2) a green-sensitive silver halide emulsion layer having operatively associated therewith a said quinonoid compound of (1) with the difference that a magenta dye is split off in diffusible state, and (3) a blue-sensitive silver halide emulsion layer having operatively associated therewith a said quinonoid compound of (1) with the difference that a yellow dye is split off in diffusible state.

11. A photographic material according to claim 1, wherein the photosensitive silver halide emulsion layer(s) is (are) negative-working and applied to the same support as a non-light-sensitive receptor layer so as to form an integral combination of light-sensitive layer(s) with the non-light-sensitive receptor layer and an opaque layer, which is alkali-permeable, reflective to light and located between the receptor layer and the silver halide emulsion layer(s).

12. A photographic material according to claim 1, characterized in that the material is a film unit that is adapted to be processed by passing said unit between a pair of juxtaposed pressure-applying members, said unit comprising (1) a photosensitive element, which contains a silver halide emulsion layer having associated therewith said quinonoid compound that is initially immobile in an alkali-permeable colloid medium and wherefrom through the reducing action of a silver halide developing agent and alkalinity a dye is split off in diffusible state, (2) an image dye-receiving layer, (3) means for discharging an alkaline processing composition within the film unit, said means being a rupturable container, which is adapted to be positioned during processing of the film so that a compressive force applied to the container by the pressure-applying members will effect a discharge of the container's contents within the film, and (4) a silver halide developing agent, which is soluble in an alkaline processing composition located within said film unit.

* * * * *